(12) United States Patent
Pelletier et al.

(10) Patent No.: US 10,527,634 B2
(45) Date of Patent: Jan. 7, 2020

(54) DIAGNOSTIC MARKERS OF COGNITIVE IMPAIRMENTS, KITS AND USES THEREOF

(71) Applicant: ADventDX, Wilmington, DE (US)

(72) Inventors: Nicolas Pelletier, Marseilles (FR);
Philippe Compagnone, Auriol (FR);
Nathalie Compagnone, Auriol (FR)

(73) Assignee: ADventDX, Wilmington, DE (US)

( * ) Notice: Subject to any disclaimer, the term of this patent is extended or adjusted under 35 U.S.C. 154(b) by 0 days.

(21) Appl. No.: 15/553,186

(22) PCT Filed: Feb. 26, 2016

(86) PCT No.: PCT/EP2016/054063
§ 371 (c)(1),
(2) Date: Aug. 24, 2017

(87) PCT Pub. No.: WO2016/135280
PCT Pub. Date: Sep. 1, 2016

(65) Prior Publication Data
US 2018/0120333 A1 May 3, 2018

(30) Foreign Application Priority Data
Feb. 26, 2015 (EP) .................................... 15156827

(51) Int. Cl.
*G01N 33/68* (2006.01)
(52) U.S. Cl.
CPC ..... *G01N 33/6896* (2013.01); *G01N 2333/52* (2013.01); *G01N 2333/5403* (2013.01); *G01N 2333/70546* (2013.01); *G01N 2800/2814* (2013.01); *G01N 2800/2821* (2013.01); *G01N 2800/52* (2013.01)

(58) Field of Classification Search
None
See application file for complete search history.

(56) References Cited

U.S. PATENT DOCUMENTS

2010/0124756 A1 5/2010 Ray et al.
2011/0274696 A1 11/2011 Gladue et al.
2014/0228240 A1 8/2014 Hu

FOREIGN PATENT DOCUMENTS

WO   WO 2007/059135   5/2007
WO   WO 2013/148708   10/2013

OTHER PUBLICATIONS

Naert et al., A deficiency in CCR2+ monocytes: the hidden side of Alzheimer's disease, 2013, Journal of Molecular Cell Biology 5: 284-293 (Year: 2013).*
Conductier, G. et al. "The role of monocyte chemoattractant protein MCP1/CCL2 in neuroinflammatory diseases" *Journal of Neuroimmunology*, Jul. 2010, pp. 93-100, vol. 224.
Laske, C. et al. "Macrophage Colony-Stimulating Factor (M-CSF) in Plasma and CSF of Patients with Mild Cognitive Impairment and Alzheimer's Disease" *Current Alzheimer Research*, Aug. 2010, pp. 409-414, vol. 7, No. 5.
Olson, L. et al. "Growth factors and cytokines/chemokines as surrogate biomarkers in cerebrospinal fluid and blood for diagnosing Alzheimer's disease and mild cognitive impairment" *Experimental Gerontology*, Jan. 2010, pp. 41-46, vol. 45, No. 1.
Quinn, J. "Biomarkers for Alzheimer's disease: Showing the way or leading us astray?" *Journal of Alzheimer's Disease*, 2013, pp. 1-6, vol. 33, Supp. 1.
Westin, K. et al. "CCL2 Is Associated with a Faster Rate of Cognitive Decline during Early Stages of Alzheimer's Disease" *PLoS ONE*, Jan. 2012, pp. 1-6, vol. 7, No. 1.
Written Opinion in International Application No. PCT/EP2016/054063, dated Apr. 19, 2016, pp. 1-8.

* cited by examiner

*Primary Examiner* — John D Ulm
(74) *Attorney, Agent, or Firm* — Saliwanchik, Lloyd & Eisenschenk

(57) ABSTRACT

The invention relates to in vitro or ex vivo methods for assessing the cognitive function of a subject in the context of the prevention of neurodegenerative diseases. A particular method comprises a step of associating a subject to a cognitive status selected from healthy cognitive status, Subjective Cognitive Impairment, Mild Cognitive Impairment and neurodegenerative disease, and the association of cognitive status results from the evaluation of glycosylated MCSF and CCR2 expressed at the surface of PBMC in a biological sample from the subject. The present invention also provides kits suitable for implementing such methods.

21 Claims, 20 Drawing Sheets

DIAGNOSTIC MARKERS OF COGNITIVE IMPAIRMENTS, KITS AND USES THEREOF

CROSS-REFERENCE TO RELATED APPLICATION

Figure 1:
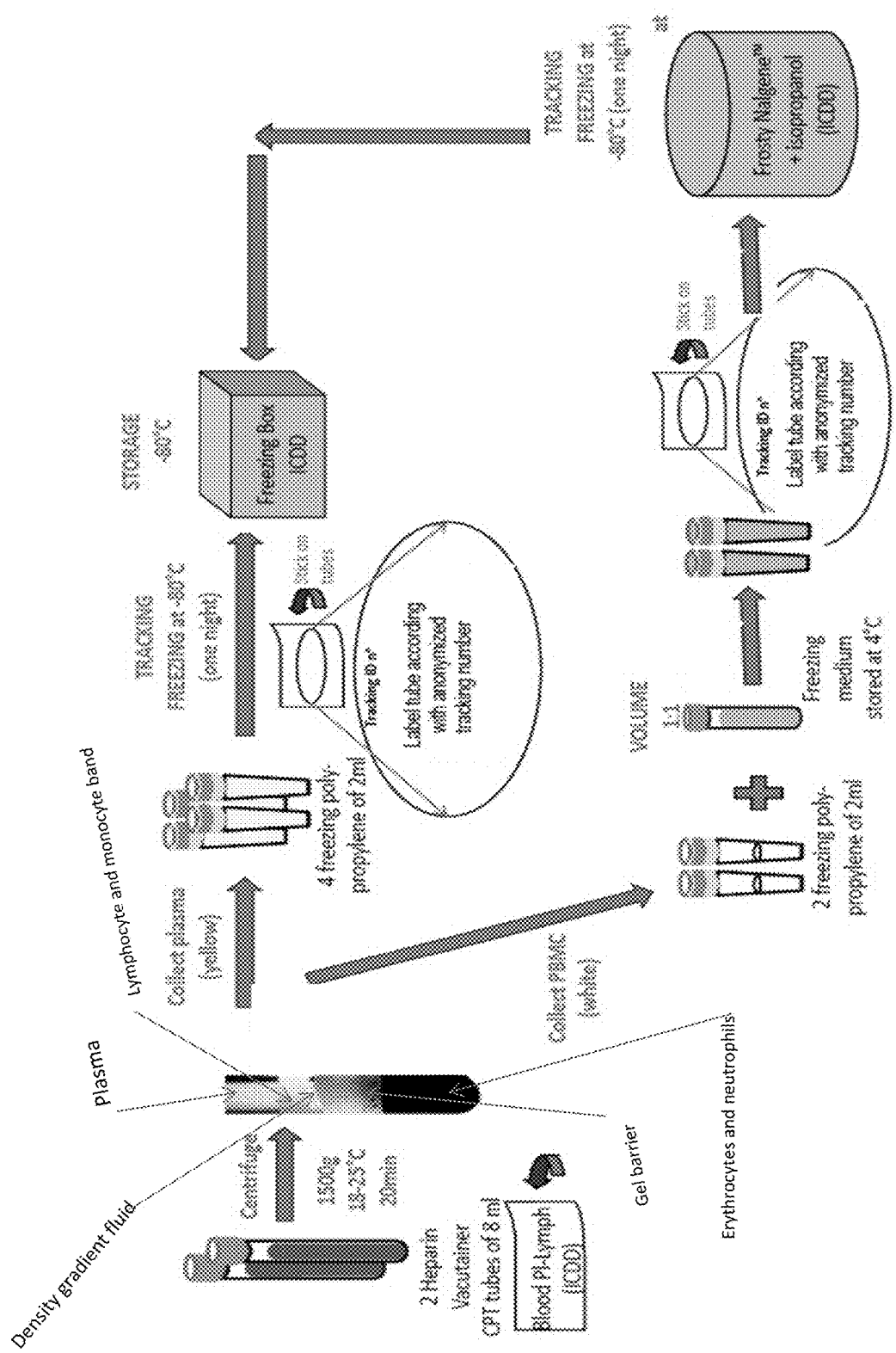

This application is the U.S. national stage application of International Patent Application No. PCT/EP2016/054063, filed Feb. 26, 2016.

FIELD OF THE INVENTION

The present disclosure generally relates to the fields of genetics and diagnostic medicine. The invention more specifically relates to an in vitro or ex vivo method for assessing the cognitive function of a subject in the context of the prevention of neurodegenerative diseases. This method comprises a step of associating a subject to a cognitive status selected from healthy cognitive status, Subjective Cognitive Impairment (SCI), Mild Cognitive Impairment (MCI), in particular early Mild Cognitive Impairment (eMCI) or late Mild Cognitive Impairment (lMCI), and neurodegenerative disease, in particular Alzheimer's disease (AD), wherein said association results from the evaluation of at least one (bio)marker, preferably at least two (bio)markers, selected from MCSF (Macrophage Colony Stimulating Factor), preferably glycosylated MCSF, CCR2 expressed at the surface of PBMC, IL-3, CCL 18 (PARC), CCL15 (MIP1delta), CD3 expressed at the surface of peripheral blood mononuclear cells (PBMC), CD11c expressed at the surface of PBMC, in particular of $CD3^+$ and/or $CD11c^+$ PBMC, and RANTES (CCL5) in a biological sample from the subject. Thanks to the present invention, it is now possible to select or distinguish in a population of subjects, at least two, for example three, subgroups of subjects respectively suffering of SCI and MCI, in particular eMCI and lMCI. The invention also discloses methods for predicting and/or assessing the cognitive status conversion of a subject, the responsiveness of a subject to a treatment against a neurodegenerative disease or the efficacy of such a treatment in a subject, as well as a method for selecting subjects eligible for a clinical study or trial for a neurodegenerative disease. The present invention in addition provides kits suitable for implementing such methods.

BACKGROUND OF THE INVENTION

"Alzheimer's disease" or "AD" is a neurodegenerative disease of the central nervous system associated with progressive memory loss. It is the most common form of senile dementia. It constitutes the 6th cause of death in the USA. 5.3 million people currently live with the disease in the USA for a global annual healthcare cost of $148 billion. In France 0.85 million people are currently diagnosed with AD. In extended European countries, including Turkey, 10.11 million patients are affected by the disease for a global annual healthcare cost of € 177 billion. The number of people affected with AD is expected to nearly double every two decades to reach 65.7 million in 2030 and 115.4 million in 2050 worldwide.

Current treatments only help with the symptoms of the disease. There are no available treatments that stop or reverse the progression of the disease. Alzheimer's disease is non-curable. The disease worsens as it progresses, patients progressively losing all autonomy, and ultimately leads to death. On average, the life expectancy following diagnosis is approximately seven years. Fewer than 3% of individuals live more than 14 years after diagnosis (Mölsä et al.; 1995).

In developed countries, AD is one of the most costly diseases to society (Bonin-Guillaume et al.; 2005). In 2006, there were 26.6 million people worldwide with AD. Alzheimer's is predicted to affect 1 in 85 people globally by 2050 (Brookmeyer et al.; 2007).

The cause and progression of the disease are not well understood. It is associated with extracellular plaques and intracellular tangles in areas of the brain essential for cognitive function (Tiraboschi et al.; 2004). Plaques are formed mostly from the deposition of amyloid beta ("Aβ"), a peptide derived from amyloid precursor protein ("APP"). Filamentous tangles are formed from paired helical filaments composed of neurofilament and hyperphosphorylated tau protein, a microtubule-associated protein. It is not clear however whether these two pathological changes are only associated with the disease or truly involved in the degenerative process.

Diagnosis of AD is long and difficult because of the lack of sensitivity of the neurological examination used in the clinic. AD develops for an unknown and variable amount of time before becoming fully apparent, and it can progress undiagnosed for years. The early stages of Alzheimer's disease are in particular very difficult to diagnose. Early symptoms are indeed often mistakenly thought to be 'age-related' concerns or manifestations of stress (Waldemar et al.; 2007) and predicting how the disease will affect a person is difficult. In the early stages, the most common symptom is difficulty in remembering recent events, known as short term memory loss.

A more accurate diagnosis is usually made once cognitive impairment compromises daily living activities, although the person may still be living independently. When AD is suspected, the diagnosis is usually refined with tests that evaluate behaviour and thinking abilities, often followed by a brain scan if available. Brain scan (CT, MRI, PET and/or SPECT scans and EEG) can indeed help excluding other cerebral pathology or subtypes of dementia.

The symptoms will progress from mild cognitive impairments ("MCI"), such as memory loss through increasing stages of cognitive and non-cognitive disturbances, eliminating any possibility of independent living, especially in the late stages of the disease (Forstl et al.; 1999). As the disease advances, symptoms can include confusion, irritability, aggression, mood swings, trouble with language, and long-term memory loss. As the person's condition declines they often withdraw from family and society. Gradually, bodily functions are lost, ultimately leading to death.

US 2010/124756 indicates that the respective levels of at least 16 circulating biomarkers are to be measured in a biological fluid sample from an individual for aiding in the diagnosis of AD and lMCI. WO2007/059135 describes methods for aiding in the diagnosis of AD and lMCI comprising detecting, measuring and/or identifying one or more of the biomarkers selected in a list comprising M-CSF and CCL18 (PARC) among other biomarkers which are not identified as relevant in the context of the present invention. As herein demonstrated by inventors, and contrary to the teaching of US 2010/124756, WO2007/059135, Laske C. et al. and Olson L. et al., the concentrations of M-CSF, CCL18 and RANTES do not linearly increase with disease progression.

Known markers for AD capable of supporting medical diagnostic at a validated stage of development include Amyloid Beta peptidic fragment 1-40 and 1-42 in blood or cerebrospinal fluid (CSF), genetic variants of the APOe4 gene, and phosphorylation status of Tau protein in CSF (cf. Laske C. et al for example). Despite a recent IVD (In Vitro Diagnostic) marking, these markers have failed to significantly penetrate the clinical practice because of the lack of robustness and reproducibility of the assays proposed. Data interpretation remains difficult and the field diverges on the actual clinical value of such markers, which remain marginally used in early stages of the disease. Diagnosis is thus mainly based on clinical criteria as well as on exclusion of other causes of dementia but a definitive diagnosis can only be made at autopsy when brain material is available and can be examined histologically.

Despite tremendous efforts and success in the development of medical imaging tools, diagnosing AD at an early stage remains a challenge. Undetected impairment in cognition has been associated with greater morbidity and mortality (Inouye et al., 2001), therefore, recognizing as early as possible the presence of impairment in cognitive functioning is becoming a crucial issue.

In addition, all drugs developed to date for AD have failed to show significant reduction in the progression rate or severity of the disease. A major impediment to the therapeutic development and clinical trial design for AD is again the lack of a sensitive, easily-obtained biomarker of disease state (O'Bryant et al., 2014, Henriksen et al., 2014, Thal et al., 2006 and Schneider et al., 2009). Recognizing the disease at an earlier stage when pathophysiological impairments have begun but their clinical manifestation is still silent will enhance the possibility for drugs targeting these mechanisms to show clinical benefit to the patient by retarding or stopping disease progression.

Furthermore, the capability to stratify patients in more homogeneous subgroups, in particular SCI, MCI and AD, will simplify clinical trials currently burdened by a highly heterogeneous patient population with the ability to design adaptive clinical trials, likely to reduce costs and length for obtaining clinical proof of concept (Chen et al., 2012).

The present invention now provide for the first time a blood protein panel to efficiently diagnose dementia, in particular Alzheimer's disease, at stages where it is not clinically expressed and in the early stages of its clinical expression.

SUMMARY OF THE INVENTION

Assessing cognitive function is the foundation for early detection and prompt treatment of impairment.

The present invention now provides new diagnostic tools involving biomarkers capable of detecting the prodrome condition of AD, i.e. the early symptom (or set of symptoms) that might indicate the start of AD, among distinct form of dementia or neurodegenerative diseases, before specific symptoms occur. These biomarkers are further advantageously capable of accurately distinguishing in a population the sub-groups of subjects suffering of Subjective Cognitive Impairment (SCI), Mild Cognitive Impairment (MCI), in particular and for example early Mild Cognitive Impairment (eMCI) and late Mild Cognitive Impairment (lMCI), or AD, and of determining among the subjects identified as suffering of SCI or MCI those who will develop an AD (vs any distinct form of dementia or neurodegenerative diseases).

In vitro or ex vivo methods for assessing the cognitive function of a subject are herein advantageously described.

A first method comprises a step of associating the subject to a cognitive status selected from Subjective Cognitive Impairment (SCI), early Mild Cognitive Impairment (eMCI) and late MCI (lMCI). This association results from the evaluation of at least one biomarker selected from MCSF (Macrophage Colony Stimulating Factor), IL-3, CCL 18 (PARC), CCL15 (MIP1delta), CD3 expressed at the surface of peripheral blood mononuclear cells (PBMC), CD11c expressed at the surface of PBMC, CCR2 expressed at the surface of PBMC (preferably CCR2 expressed at the surface of $CD3^+$ and/or $CD11c^+$ PBMC), and optionally RANTES (CCL5) in a biological sample from the subject.

A second method comprises a step of associating the subject to a cognitive status selected from Subjective Cognitive Impairment (SCI) and Mild Cognitive Impairment (MCI). This association results from the evaluation of at least glycosylated MCSF (Macrophage Colony Stimulating Factor) and CCR2 expressed at the surface of peripheral blood mononuclear cells (PBMC), preferably together with at least one of IL-3 and CCL18 (PARC), for example together with IL-3 and CCL18, in a biological sample from the subject. In another embodiment, the association results from the additional evaluation of CCL15 (MIP1-delta) and/or RANTES (CCL5).

These first and second methods, may further advantageously comprise a step of selecting among the PBMC present in the biological sample from the subject those expressing at least one, preferably at least two, even more preferably three, surface marker(s) selected from CD3, CD11c, CD14, CD4, CD8, CD25, CD27, CD33, CD38, CD62L, CD45RO, CD123, CD127, CD131, CD163, CD196 (CCR7) and CXCR3, and a step of evaluating CCR2 in the selected PBMC.

These methods are typically implemented in:
  a method for selecting in a population of subjects, at least two, for example three, subgroups of subjects respectively suffering of Subjective Cognitive Impairment (SCI) and Mild Cognitive Impairment (eMCI), in particular and for example early Mild Cognitive Impairment (eMCI) and late MCI (lMCI),
  a method for selecting subjects eligible for a clinical study or trial for a neurodegenerative disease,
  a method for predicting and/or assessing the responsiveness of a subject to a treatment against a neurodegenerative disease, or the efficacy of such a treatment in a subject, and
  a method for selecting the appropriate anti-inflammatory drug for preventing or treating a cognitive impairment selected from SCI and MCI, in particular and for example eMCI and lMCI, in a subject.

Another objet of the invention relates to an in vitro or ex vivo method for assessing the cognitive function of a subject, wherein said method comprises a step a) of determining whether said subject is suffering of Subjective Cognitive Impairment (SCI), said step a) comprising evaluating at least CCR2 expressed at the surface of PBMC in a biological sample from the subject, and if the subject is not identified as suffering of SCI, a step b) of determining whether said subject is suffering of Mild Cognitive Impairment (MCI) said step b) comprising evaluating glycosylated MCSF, preferably glycosylated MCSF together with CCL18, and optionally together with CCR2, in the biological sample from the subject and if the subject is not identified as suffering of MCI, a step c) of determining whether said subject is suffering of AD, said step c) comprising evaluating CCL-18 and IL3 in the biological sample from the subject.

A further object of the invention relates to an in vitro or ex vivo method for assessing the cognitive function of a subject, wherein said method comprises a step of measuring the ratio of glycosylated MCSF over non glycosylated MCSF in a biological sample from the subject, a ratio below 1 being indicative of a AD status, and a ratio above 1 being indicative of a predementia status, such as a MCI or SCI status.

Also herein described is a kit comprising at least one, preferably at least two, reagent(s) specific for at least one of the following biomarkers: MCSF (Macrophage Colony Stimulating Factor), IL-3, CCL 18 (PARC), CCL15 (MIP1delta), CD3 expressed at the surface of peripheral blood mononuclear cells (PBMC), CD11c expressed at the surface of PBMC, CCR2 expressed at the surface of PBMC (preferably CCR2 expressed at the surface of $CD3^+$ and/or $CD11c^+$ PBMC), and optionally RANTES (CCL5); and instructions for carrying out the method.

Further herein described is a kit comprising at least one, preferably at least two, reagent(s) specific for each of at least glycosylated MCSF and CCR2 expressed at the surface of PBMC, and preferably in addition at least one, preferably at least two, reagent(s) specific for at least one of IL-3 and CCL18 (PARC), for example for each of IL-3 and CCL18; and instructions for carrying out the method.

These kits are advantageously suitable for implementing a method for assessing the cognitive function of a subject, or for determining whether a subject is suffering of a cognitive impairment or of a neurodegenerative disease, or is at risk of developing such a neurodegenerative disease, in particular the Alzheimer's disease.

Also herein described are a kit for assessing whether a subject suffering of SCI or MCI is at risk of developing AD, wherein the kit comprises at least one, preferably at least two, reagent(s) specific for each of at least CCR2 expressed at the surface of PBMC and glycosylated MCSF, and a kit for assessing whether a subject is suffering of AD, wherein the kit comprises at least one, preferably at least two, reagent(s) specific for each of at least CCL18 and IL3, preferably for each of at least CCL18, IL3, CCR2 and CCL15.

DETAILED DESCRIPTION OF THE INVENTION

The Alzheimer's disease course is classically divided into four to seven stages, with progressive patterns of cognitive and functional impairments. Pre-dementia (preclinical stage of the disease), early stage of AD, moderate stage of AD and Advanced stage of AD are at least distinguished. Subjective Cognitive Impairment (SCI) and Mild Cognitive Impairment (MCI) are frequently seen as prodromal stages of AD which overlap with, or are included in, the "Pre-dementia" stage (preclinical stage of the disease). As such, if detected early, they represent the best opportunity for pharmaceutical intervention.

"Subjective Cognitive Impairment" (SCI) is characterized by subjective decline in memory and functioning but does not meet the clinical definition of MCI, in which subtle changes may become visible to observers and cognitive impairment is elicited with testing. SCI typically defines a subject who has been assessed with the MMSE and scored at or above 28 or who has been assessed with the ADAS-Cog (11 items) and scored between 8-5 (not above 8), or who would achieve such a score upon MMSE or ADAS-Cog testing.

"Mild Cognitive Impairment" (MCI, also known as incipient dementia, or isolated memory impairment) commonly designates a brain function syndrome involving the onset and evolution of cognitive impairments beyond those expected based on the age and education of the individual, but which are not significant enough to interfere with their daily activities (Petersen et al.; 1999). Mild cognitive impairment may increase your risk of later progressing to dementia, caused by Alzheimer's disease or other neurological conditions. But some people with mild cognitive impairment never get worse, and a few eventually get better.

The clinical criteria used for diagnosis of Mild Cognitive Impairment (MCI) are those of Peterson et al. (1999) and include: 1) memory complaints corroborated by an informant, 2) objective memory impairment for age and education, 3) normal general cognitive function, 4) intact activities of daily living, and 5) the subject does not meet criteria for dementia.

MCI also defines a subject who has been assessed with the MMSE and scored at or above 23 or who has been assessed with the ADAS-Cog (11 items) and scored between 12-15 (not above 15), or who would achieve such a score upon MMSE or ADAS-Cog testing.

Although MCI can present with a variety of symptoms, when memory loss is the predominant symptom it is termed "amnestic MCI" and is frequently seen as a prodromal stage of Alzheimer's disease. Studies suggest that these individuals tend to progress to probable Alzheimer's disease at a rate of approximately 10% to 15% per year (Grundman et al.; 2004).

The terms "neurodegenerative disease" typically refers to dementia, in particular to Alzheimer's disease (AD).

Inventors now provide an in vitro or ex vivo method for assessing the cognitive function of a subject. This method comprises a step of associating the tested subject to a cognitive status selected from Subjective Cognitive Impairment (SCI) and Mild Cognitive Impairment (MCI), in particular and for example early Mild Cognitive Impairment (eMCI) and late MCI (lMCI). This association results from the evaluation of at least one biomarker, for example at least two, three, four or five biomarkers, for example six biomarkers, selected from MCSF (Macrophage Colony Stimulating Factor), in particular glycosylated MCSF, CCR2 expressed at the surface of PBMC (preferably CCR2 expressed at the surface of $CD3^+$ and/or $CD11c^+$ PBMC), IL-3, CCL 18 (PARC), CCL15 (MIP1delta), CD3 expressed at the surface of peripheral blood mononuclear cells (PBMC), CD11c expressed at the surface of PBMC, and optionally RANTES (CCL5 or Chemokine (C—C motif) ligand 5), in a biological sample from the subject, preferably selected from MCSF, IL-3, CCL 18, CCL15 and CCR2 expressed at the surface of PBMC (preferably CCR2 expressed at the surface of $CD3^+$ and/or $CD11c^+$ PBMC). The association preferably results from the evaluation of at least two biomarkers, namely CCR2 expressed at the surface of PBMC (preferably CCR2 expressed at the surface of $CD3^+$ and/or $CD11c^+$ PBMC) and MCSF, or at least three biomarkers, namely CCR2 expressed at the surface of PBMC (preferably CCR2 expressed at the surface of $CD3^+$ and/or $CD11c^+$ PBMC), MCSF and IL3.

Other biomarkers of interest include the proportion of $CD3^+$ and/or $CD11c^+$ circulating PBMC amongst total circulating PBMC. Typical $CD3^+$ PBMC are $CD3^+$ T cells or $CD3^+$ B cells. Typical $CD11c^+$ PBMC are $CD11c^+$ macrophages or $CD11c^+$ dendritic cells (DC).

Inventors also herein provide an in vitro or ex vivo method for assessing the cognitive function of a subject which comprises a step of associating said subject to a cognitive status selected from Subjective Cognitive Impairment (SCI) and Mild Cognitive Impairment (MCI), in particular and for example early Mild Cognitive Impairment (eMCI) and late MCI (lMCI), and wherein said association results from the evaluation of glycosylated MCSF (Macrophage Colony Stimulating Factor) and CCR2 expressed at the surface of peripheral blood mononuclear cells (PBMC), and preferably at least one of IL-3 and CCL18 (PARC), for example together with IL-3 and CCL18, in a biological sample from the subject. In a particular embodiment, the association results from the additional evaluation of CCL15 (MIP1-delta) and/or RANTES (CCL5).

The herein described methods, may further advantageously comprise a step of selecting among the PBMC present in the biological sample from the subject those expressing at least one, preferably at least two, even more preferably three, surface marker(s) selected from CD3, CD11c, CD14, CD4, CD8, CD25, CD27, CD33, CD38, CD62L, CD45RO, CD123, CD127, CD131, CD163, CD196 (CCR7) and CXCR3, and a step of evaluating CCR2 in the selected PBMC.

Another objet of the invention relates to an in vitro or ex vivo method for assessing the cognitive function of a subject, wherein said method comprises a step a) of determining whether said subject is suffering of Subjective Cognitive Impairment (SCI), said step a) comprising evaluating at least CCR2 expressed at the surface of PBMC in a biological sample from the subject, and if the subject is not identified as suffering of SCI, a step b) of determining whether said subject is suffering of Mild Cognitive Impairment (MCI) said step b) comprising evaluating glycosylated MCSF, preferably glycosylated MCSF together with CCL18, and optionally together with CCR2, in the biological sample from the subject, and if the subject is not identified as suffering of MCI, a step c) of determining whether said subject is suffering of AD, said step c) comprising evaluating CCL-18 (PARC) and IL3 in the biological sample from the subject.

A further objet of the invention relates to an in vitro or ex vivo method for assessing the cognitive function of a subject, wherein said method comprises a step of measuring the ratio of glycosylated MCSF/non glycosylated MCSF in a biological sample from the subject, a ratio below 1 being indicative of a AD status, and a ratio above 1 being indicative of predementia status, such as a MCI or SCI status.

The term "biological sample" includes any biological sample from a subject, in particular a mammalian subject, typically a human being. The biological sample may be a biological fluid sample or a tissue biopsy. It is preferably a biological fluid sample.

Typical examples of biological fluid samples usable in the context of the present invention may be selected from blood, plasma, serum and peripheral blood mononuclear cells (PBMC) in particular macrophages, dendritic cells, T lymphocytes and/or B lymphocytes, preferably PBMC expressing at least one, preferably at least two, even more preferably three, surface marker(s) selected from CD3, CD11c, CD14, CD4, CD8, CD25, CD27, CD33, CD38, CD62L, CD45RO, CD123, CD127, CD131, CD163, CD196 (CCR7) and CXCR3, preferably PBMC expressing CD11c, CD3 and/or CD14, for example CD3$^+$CD11c$^+$ PBMC, CD3$^+$CD14$^+$ PBMC, CD11c$^+$CD14$^+$ PBMC, or CD3$^+$CD11c$^+$CD14$^+$ PBMC. The biological sample is typically a blood sample, preferably a whole blood sample, i.e. a blood sample comprising plasma and circulating PBMC. A particular blood sample is a sample deprived of red blood cells only.

The definition also includes samples that have been manipulated in any way after their procurement, such as by treatment with reagents, solubilization, or enrichment for certain components, such as proteins or polynucleotides.

The term "subject" refers to any testable subject and typically designates a patient. Preferably the subject is a mammal, even more preferably a human being. The subject may be tested whatever his/her age or sex.

The invention may be used both for an individual and for an entire population.

The subject can be a subject at risk, or suspected to be at risk, of developing a specific neurodegenerative disease, for example a subject with a familial history of dementia, for example of Alzheimer's disease.

The subject can be asymptomatic, or present early or advanced signs of such a disease. Typically the subject is asymptomatic or present early signs of such a disease. Typically the subject exhibits no disease symptom but is eligible for a clinical study or trial concerning a neurodegenerative disease.

The subject can be an individual presenting at least one symptom of SCI or MCI (for example eMCI or lMCI), and is for example selected from an individual exhibiting a behavior that is unusual and/or inappropriate to the situation, such as family history of mental illness, memory loss, confusion, irritability, aggression, mood swings and/or trouble with language as described herein in the background part.

The terms "SCI subject" refer to an individual who has been diagnosed with Subjective Cognitive Impairment or has been given a probable diagnosis of Subjective Cognitive Impairment.

The terms "eMCI subject" refer to an individual who has been diagnosed with early Mild Cognitive Impairment or has been given a probable diagnosis of early Mild Cognitive Impairment.

The terms "lMCI subject" refer to an individual who has been diagnosed with late Mild Cognitive Impairment or has been given a probable diagnosis of late Mild Cognitive Impairment.

The terms "Alzheimer's patient", "AD patient", "AD subject" or "diseased subject" refer to an individual who has been diagnosed with AD or has been given a probable diagnosis of AD.

The term "Diagnostic" refers to the detection or identification of a disease, such as AD, of a disorder such as a cognitive impairment as herein described. The term "Diagnostic" also refers to the evaluation (dosing, comparison) of the severity or of the progression of such a disease or disorder in a subject as herein defined. The term "Diagnostic" thus also refers to the detection, assessment or identification of the cognitive status of a subject, said status being selected from SCI, MCI, for example eMCI and lMCI, and AD as herein defined.

In particular, a diagnostic method of the invention comprises the evaluation, i.e. determination of the presence and/or the measure of the quantity of at least one (bio) marker as herein identified, for example selected from MCSF, preferably glycosylated MCSF, IL-3, CCL18, CCL15, CD3 expressed at the surface of peripheral blood mononuclear cells (PBMC), CD11c expressed at the surface of PBMC, CCR2 expressed at the surface of PBMC (preferably CCR2 expressed at the surface of CD3$^+$ and/or CD11c$^+$ PBMC) and optionally RANTES, in a biological sample from the subject. In an embodiment, the selected (bio)markers are glycosylated MCSF and CCR2 expressed at the surface of PBMC.

In another embodiment, the selected (bio)markers are glycosylated MCSF and CCR2 expressed at the surface of PBMC, and preferably at least one of IL-3 and CCL18 (PARC), for example both IL-3 and CCL18.

In a further embodiment, the selected (bio)markers are glycosylated MCSF and CCR2 expressed at the surface of PBMC, preferably together with at least one of IL-3 and CCL18 (PARC), for example both IL-3 and CCL18, and even more preferably together with CCL15 (MIP1-delta) and/or RANTES (CCL5), for example both CCL15 and RANTES.

In these contexts, the expression of CCR2 is preferably assessed on PBMC expressing at least one, preferably at least two, even more preferably three, surface marker(s) selected from CD3, CD11c, CD14, CD4, CD8, CD25, CD27, CD33, CD38, CD62L, CD45RO, CD123, CD127, CD131, CD163, CD196 (CCR7) and CXCR3. Even more preferred selected (isolated) PBMC express CD11c, CD3 and/or CD14.

The evaluation provides valuable information for assessing the cognitive status of the subject, for predicting the stage of cognitive impairment conversion (progression or regression of the disease or disorder) within a SCI, a MCI, for example within a eMCI and a lMCI, and a neurodegenerative disease, for assessing the responsiveness of the subject to a therapeutic or prophylactic treatment, or the efficacy of such a treatment in the subject.

The evaluation preferably comprises the comparison of the quantity/concentration of each biomarker to a reference value, and a comparison of the biomarkers relative to each other, for example through a ratio, when at least two, preferably at least three or four, for example five or six, biomarkers are evaluated. More precisely, the presence (versus absence) of this at least one biomarker, or a deviation from, or an adequation with, the reference value, typically the presence of this at least one biomarker in a quantity distinct or different from (below or above) the reference value, in the biological sample of the subject, provides valuable information to assess the cognitive status of the subject, the conversion of a subject's status from a determined status to a distinct status, the responsiveness of the subject to a therapeutic or prophylactic treatment, or the efficacy of such a treatment.

The method of the invention is typically implemented in:
  a method for selecting in a population of subjects, at least two, for example three, subgroups of subjects respectively suffering of Subjective Cognitive Impairment (SCI) and Mild Cognitive Impairment (MCI), for example SCI, early Mild Cognitive Impairment (eMCI) and late MCI (lMCI),
  a method for selecting subjects eligible for a clinical study or trial for a neurodegenerative disease,
  a method for predicting and/or assessing the responsiveness of a subject to a treatment against a neurodegenerative disease, or the efficacy of such a treatment in a subject,
  a method for predicting and/or assessing the cognitive impairment progression (course) of a subject within a Subjective Cognitive Impairment (SCI), a Mild Cognitive Impairment (MCI), for example an early Mild Cognitive Impairment (eMCI) or a late MCI (lMCI), and a neurodegenerative disease, and
  a method for selecting the appropriate anti-inflammatory drug for preventing or treating a cognitive impairment selected from SCI, MCI, for example eMCI or lMCI, and neurodegenerative disease in a subject.

The term "Prediction" refers to the evaluation/assessment or monitoring of the cognitive impairment progression (course) within a Subjective Cognitive Impairment (SCI), a Mild Cognitive Impairment (MCI), in particular for example early Mild Cognitive Impairment (eMCI) or late MCI (lMCI), and a neurodegenerative disease, for example Alzheimer's disease (as herein described), in a subject (as herein defined), treated or not, typically the prediction of the worsening of such an impairment or disease or, on the contrary, the prediction of an improvement of the subject's health.

A particular method herein described comprises the following steps of:
  formulating a decision tree, and of
  using the decision tree for selecting the additional (bio) marker(s) to evaluate in the biological sample of the tested subject (or population of subjects), wherein said evaluation aids in assessing the cognitive status of the tested subject and in predicting the cognitive impairment progression within a SCI, a MCI (for example within a eMCI and a lMCI) and a neurodegenerative disease, preferably AD.

A predicting method of the invention can comprise one or several steps of monitoring, dosing, comparing the measured quantity(ies) or level(s) of at least one biomarker as herein identified, preferably several biomarkers as herein identified, for example selected from MCSF (Macrophage Colony Stimulating Factor), IL-3, CCL 18 (PARC), CCL15 (MIP1delta), CD3 expressed at the surface of peripheral blood mononuclear cells (PBMC), CD11c expressed at the surface of PBMC, CCR2 expressed at the surface of peripheral blood mononuclear cells (PBMC), in particular CCR2 expressed at the surface of CD3$^+$ and/or CD11c$^+$ PBMC, and optionally RANTES (CCL5), at various stages, including, pre-symptomatic stages, early and late stages, in a biological sample or in biological samples from the subject.

In an embodiment, the selected (bio)markers are glycosylated MCSF and CCR2 expressed at the surface of PBMC.

In another embodiment, the selected (bio)markers are glycosylated MCSF and CCR2 expressed at the surface of PBMC, and preferably at least one of IL-3 and CCL18 (PARC), for example both IL-3 and CCL18.

In a further embodiment, the selected (bio)markers are glycosylated MCSF and CCR2 expressed at the surface of PBMC, preferably together with at least one of IL-3 and CCL18 (PARC), for example both IL-3 and CCL18, and even more preferably together with CCL15 (MIP1-delta) and/or RANTES (CCL5), for example both CCL15 and RANTES.

In these contexts, the expression of CCR2 is preferably assessed on PBMC expressing at least one, preferably at least two, even more preferably three, surface marker(s) selected from CD3, CD11c, CD14, CD4, CD8, CD25, CD27, CD33, CD38, CD62L, CD45RO, CD123, CD127, CD131, CD163, CD196 (CCR7) and CXCR3. Even more preferred selected (isolated) PBMC express CD11c, CD3 and/or CD14.

Prediction typically includes the assessment of the progression of a cognitive impairment associated with high-risk of developing AD, and the characterization of a subject to define the most appropriate treatment.

As used herein, a "reference value" or "control value" can be an absolute value; a relative value; a value that has an upper and/or lower limit; a range of values; an average value; a median value; a mean value; a statistic value; a cut-off or discriminating value; or a value as compared to a particular control or baseline value.

A reference value can be based on an individual sample value, such as for example, a value obtained from a sample from the individual tested but at an earlier point in time, or a value obtained from a sample from a subject other than the individual tested (also herein identified as "other", typically identified as a "SCI subject", "MCI subject", "eMCI subject" or "lMCI subject"), or a "normal" individual that is an individual identified has having a healthy status or an individual not diagnosed with any of MCI, for example eMCI or lMCI, or AD status.

The reference value identifies the sub-population with a predetermined specificity and/or a predetermined sensitivity based on an analysis of the relation between the parameter values and the known clinical data of the reference population (which can be for example a healthy, SCI, MCI, eMCI, lMCI or AD control population, or any other control population diagnosed with an identified dementia distinct of AD, and which is clearly identified as such whatever its nature) and of the population of the subjects of interest (which can be for example a SCI, MCI, eMCI, lMCI or AD sub-population or a population consisting in mixed subpopulations of SCI, MCI, eMCI, lMCI, AD and/or any dementia distinct of AD). The discriminating values determined in this manner are valid for the same experimental setup in future individual tests.

Typically, the accuracy of the test to discriminate diseased cases from normal cases, or a stage of cognitive impairment from another one, may be evaluated using Receiver Operating Characteristic (ROC) curve analysis (Metz, 1978; Zweig & Campbell, 1993). In signal detection theory, a ROC curve, is a graphical plot of the sensitivity (or true positive rate), vs. false positive rate (1−specificity or 1−true negative rate), for a binary classifier system. Each point on the ROC plot represents a sensitivity/specificity pair corresponding to a particular decision threshold. The area under the ROC curve is a measure of how well a parameter can distinguish between two diagnostic groups ("diseased"/"normal", "diseased"/"other", "diseased/MCI", "diseased"/"lMCI", "lMCI"/"eMCI" or "eMCI"/"normal").

In other words, "specificity" is defined as the proportion of positives (i.e. individuals having a parameter representing the concentration of a particular biomarker as herein defined in body fluid samples different, typically higher, than a predefined reference level) that are correctly identified by the described method of the invention and "sensitivity" is defined as the proportion of negatives (i.e. individuals having a parameter representing the concentration of a particular biomarker in body fluid samples different, typically lower, than a predefined reference level) that are correctly identified by the described method.

For example, the reference value can be expressed as a concentration of the biomarker in the biological sample of the tested subject for a particular specificity and/or sensitivity, or can be a normalized cut-off value expressed as a ratio for a particular specificity and/or sensitivity.

If a higher or lower sensitivity and/or specificity is/are desired, the cut-off value can easily be changed by the skilled person, for example using a different reagent for a particular biomarker.

In very specific and exemplary experimental setups, discriminating values were statistically established by inventors for the following biomarkers of interest which are to be considered individually or in combination (combination of two, three, four, five or six biomarkers):

IL-3:
   a IL-3 blood sample concentration below about 0.8 ng/ml is associated to SCI or MCI, and
   a IL-3 blood sample concentration above about 1 or 1.5 ng/ml is associated to eMCi or AD;

CCL15 (MIP1-delta):
   a CCL15 blood sample concentration below about 6 ng/ml is associated to SCI,
   a CCL15 blood sample concentration between about 6 ng/ml and 10 ng/ml is associated to SCI or early MCI,
   a CCL15 blood sample concentration between 10 ng/ml and 14 ng/ml, typically bellow 14 ng/ml, is associated to early MCI,
   a CCL15 blood sample concentration of 14 ng/ml or between 14 ng/ml and about 16 ng/ml is associated to late MCI or AD, and
   a CCL15 blood sample concentration above 16 ng/ml is associated to AD;

MCSF:
   a MCSF blood sample concentration below about 10 or below about 15 pg/ml is associated to SCI or early MCI,
   a MCSF blood sample concentration above about 25 or about 32 pg/ml is associated to late MCI, and
   a MCSF blood sample concentration between about 15 pg/ml and 28 pg/ml is associated to AD;

CCL18 (PARC):
   A CCL18 blood sample concentration below about 43 ng/ml is associated to early MCI or AD,
   a CCL18 blood sample concentration between about 43 ng/ml and 75 ng/ml is associated to early MCI,
   a CCL18 blood sample concentration above 75 ng/ml is associated to SCI or late MCI, and
   a CCL18 blood sample concentration above about 145 ng/ml, typically above 166 ng/ml is associated to late MCI;

CCR2:
   a proportion of PBMC expressing CCR2, in particular in $CD3^+$ T cells, below 0.4% is associated to AD,
   a proportion of PBMC expressing CCR2, in particular in $CD3^+$ T cells, above 0.4% and below 10-16% is associated to late MCI or SCI,
   a proportion of PBMC expressing CCR2, in particular in $CD3^+$ T cells, above 14-20% is associated to early MCI,
   a proportion of PBMC expressing CD3, in particular of $CD3^+$ T cells, equal to or above 60%, typically above 69%, is associated to late MCI or AD,
   a proportion of PBMC expressing CD3, in particular of $CD3^+$ T cells, below 54%, typically between 50 and 54%, is associated to SCI or early MCI,
   a proportion of PBMC expressing CD3, in particular of $CD3^+$ T cells, equal to or below 40%, is associated to SCI,
   a proportion of PBMC expressing CD11c, in particular of $CD11c^+$ dendritic cells or circulating monocytes, equal to or above 54% exclude early MCI,
   a proportion of PBMC expressing CD11c, in particular of $CD11c^+$ dendritic cells or circulating monocytes, above 65-70% is associated to AD, and
   a proportion of PBMC expressing CCR2, in particular of $CD11c^+$ dendritic cells or circulating monocytes, above 20-25% is associated to SCI or early MCI.

In the context of a population of subjects to be tested, an iterative classification allows the selection of subsets/groups of subjects based in a first step on the analysis of a single (bio)marker as herein described, and then in subsequent(s) step(s) on the analysis of a distinct (bio)marker or of a combination of (bio)markers as herein described, until homogeneous (statistically significant) groups of subjects are obtained and, as a consequence, correctly associated to a cognitive status selected from Subjective Cognitive Impairment (SCI), Mild Cognitive Impairment (MCI), for example early Mild Cognitive Impairment (eMCI) and/or late MCI (lMCI), and Alzheimer disease (AD).

Other experimental setups and other parameters will result in other values which can be determined in accordance with the teachings herein provided.

To determine the strength of an association between the measure of a particular biomarker or combination of biomarkers in a biological sample of a subject and the risk for the subject to develop a cognitive status as herein described or a neurodegenerative disease, in particular AD, an odd ratio may be calculated. A predictive positive value [risk of developing the cognitive status or disease in the presence of the (bio)marker or combination of (bio)markers] and a negative one [risk of developing the disease in the absence of the (bio)marker or combination of (bio)markers] can also be evaluated.

In order to assess the evolution of a disease or control the efficiency of the treatment, testing a patient and testing one additional time or several times the same patient for example several days, weeks, months or years later, typically several months later, can be of help. In such a situation, the results (measured value(s)) of the second/subsequent(s) test(s) are compared with the results of the first/previous test(s).

A quantity of biomarker "above the control value" or "higher than the control value", or on the contrary "below the control value", may mean a significant statistical increase, for example of at least 2 standard deviations.

In a particular aspect, the assessment of the cognitive function of the subject suspected of suffering of a SCI comprises the evaluation of at least one (bio)marker selected from CD3, MCSF, preferably glycosylated MCSF, IL3, CCL18, and optionally RANTES (CCL5) and/or CCR2, typically CCR2 expressed at the surface of CD3$^+$ and/or CD11c$^+$ PBMC. In a preferred embodiment, the assessment of the cognitive function of the subject suspected of suffering of a SCI comprises the evaluation of CCR2 expressed at the surface of PBMC, typically at the surface of PBMC expressing at least one, preferably at least two, even more preferably three, surface marker(s) selected from CD3, CD11c, CD14, CD4, CD8, CD25, CD27, CD33, CD38, CD62L, CD45RO, CD123, CD127, CD131, CD163, CD196 (CCR7) and CXCR3, preferably from CD11c, CD3 and/or CD14.

In a particular aspect, the assessment of the cognitive function of the subject suspected of suffering of a eMCI comprises the evaluation of at least one (bio)marker selected from MCSF, preferably glycosylated MCSF, CCL15, CD11c, and CCR2, in particular CCR2 expressed at the surface of CD3$^+$ and/or CD11c$^+$ PBMC, and optionally IL3 and/or CCL18. In a preferred embodiment, the assessment of the cognitive function of the subject suspected of suffering of a eSCI comprises the evaluation of glycosylated MCSF.

In a particular aspect, the assessment of the cognitive function of the subject suspected of suffering of a lMCI comprises the evaluation of at least one (bio)marker selected from CD11c expressed at the surface of PBMC, MCSF, preferably glycosylated MCSF, CCL15, CCL18 and optionally CCR2 expressed at the surface of PBMC. In a particular embodiment, CCR2 and CCL15 at least are evaluated. In a preferred embodiment, the assessment of the cognitive function of the subject suspected of suffering of a lSCI comprises the evaluation of glycosylated MCSF, CCL18, and optionally CCR2.

In a particular aspect, the assessment of the cognitive function of the subject suspected of suffering of AD comprises the evaluation of at least one (bio)marker selected from CD11c and/or CD3 expressed at the surface of PBMC, MCSF, preferably glycosylated MCSF, CCL15, CCL18 and optionally RANTES (CCL5) expressed at the surface of PBMC. In a preferred embodiment, the assessment of the cognitive function of the subject suspected of suffering of AD comprises the evaluation of CCL18 and/or IL3, even more preferably each of CCL18 and IL3, and optionally CCR2 and/or CCL15. In a particular embodiment, the assessment of the cognitive function of the subject suspected of suffering of AD comprises the evaluation of CCL18, IL3, CCR2 and CCL15.

Another object herein described is a kit comprising at least one, preferably at least two, for example three, four, five or six, reagent(s) specific for at least one of the following biomarkers: MCSF (Macrophage Colony Stimulating Factor), IL-3, CCL 18 (PARC), CCL15 (MIP1delta), CCR2, CD3 expressed at the surface of PBMC, CD11c expressed at the surface of PBMC (preferably CCR2 expressed at the surface of CD3$^+$ and/or CD11c$^+$ PBMC), and optionally RANTES (CCL5), preferably specific for at least one of the following biomarkers: MCSF, IL-3, CCL 18, CCL15, and CCR2 expressed at the surface of PBMC (preferably CCR2 expressed at the surface of CD3$^+$ and/or CD11c$^+$ PBMC), even more preferably from at least glycosylated MCSF and CCR2 expressed at the surface of PBMC, preferably together with at least one of IL-3 and CCL18 (PARC), for example together with both IL-3 and CCL18 (PARC), optionally together with anyone of CCL15 (MIP1-delta) and RANTES (CCL5) or with both CCL15 and RANTES; and preferably instructions for carrying out the herein described methods.

A particular kit comprises at least one, preferably at least two, reagent(s) specific for each of the following biomarkers: glycosylated MCSF, CCR2 expressed at the surface of PBMC, IL-3, CCL18 (PARC), CCL15 (MIP1-delta) and RANTES (CCL5); and preferably instructions for carrying out the herein described methods.

When the kit comprises at least one reagent specific for CCR2 expressed at the surface of PBMC, said PBMC preferably expresses a surface marker selected from anyone of CD3, CD11c, CD14, CD4, CD8, CD25, CD27, CD33, CD38, CD62L, CD45RO, CD123, CD127, CD131, CD163, CD196 (CCR7), CXCR3 and a combination thereof, in particular a combination of at least two of CD3, CD11c and CD14.

These kits are advantageously suitable for implementing a method for assessing the cognitive function of a subject, for determining whether a subject is suffering of a cognitive impairment or of a neurodegenerative disease, or is at risk of developing such a neurodegenerative disease, in particular the Alzheimer's disease, for predicting and/or assessing the cognitive impairment progression (course) of a subject within a Subjective Cognitive Impairment (SCI), a Mild Cognitive Impairment (MCI), for example within an early Mild Cognitive Impairment (eMCI) and a late MCI (lMCI), and a neurodegenerative disease.

In particular embodiments of the invention:
  when the cognitive status of the subject has been previously identified as SCI, the kit comprises at least one reagent specific for each of at least CD3, MCSF, IL3, CCL18, and optionally RANTES (CCL5) and/or CCR2, typically CCR2 expressed at the surface of CD3$^+$ and/or CD11c$^+$ PBMC;
  when the cognitive status of the subject has been previously identified as eMCI, the kit comprises at least one reagent specific for each of at least MCSF, CCL15, CD 11c expressed at the surface of PBMC and CCR2, in particular CCR2 expressed at the surface of CD3$^+$ and/or CD11c$^+$ PBMC, and optionally IL3 and/or CCL18;

when the cognitive status of the subject has been previously identified as lMCI, the kit comprises at least one reagent specific for each of at least CD11c expressed at the surface of PBMC, MCSF, CCL15, CCL18 and CCR2 expressed at the surface of PBMC: and when the cognitive status of the subject has been previously identified as AD, the kit comprises at least one reagent specific for each of at least CD11c expressed at the surface of PBMC, IL3, CD3 expressed at the surface of PBMC, CCL18 and CCR2 expressed at the surface of PBMC.

Also herein described is a kit for assessing whether a subject suffering of SCI or MCI, for example eMCI or lMCI, is at risk of developing AD, wherein the kit comprises at least one reagent specific for each of at least CCR2 expressed at the surface of PBMC and glycosylated MCSF. Again, PBMC is preferably a PBMC expressing a surface marker selected from anyone of CD3, CD11c, CD14, CD4, CD8, CD25, CD27, CD33, CD38, CD62L, CD45RO, CD123, CD127, CD131, CD163, CD196 (CCR7), CXCR3 and a combination thereof, in particular a combination of at least two of CD3, CD11c and CD14.

Further herein described is a kit for assessing whether a subject is suffering of AD, wherein the kit comprises at least one reagent specific for each of at least CCL18 and IL3, preferably for each of at least CCL18, IL3, CCR2 and CCL15.

Whatever the herein described method, the reagent is typically selected from a capture agent binding its specific (bio)marker, for example an antibody or a fragment thereof capable of specifically binding the (bio)marker; a nucleic acid fragment having an affinity for the targeted protein; a genetically modified organisms including intracellular or secreted endosomal vesicles expressing a selected antigen; and any appropriate detecting tool allowing signal detection.

In a preferred embodiment, the kit further comprises a solid support (affinity or capture support such as magnetic beads for example) comprising the at least one capture agent attached thereto.

The herein described kits can further comprise a set or sets of reference values for a set of (bio)markers comprising at least one (bio)marker selected from MCSF (Macrophage Colony Stimulating Factor), IL-3, CCL 18 (PARC), CCL15 (MIP1delta), CD3 expressed at the surface of PBMC, CD11c expressed at the surface of PBMC, CCR2 expressed at the surface of PBMC (preferably CCR2 expressed at the surface of CD3$^+$ and/or CD11c$^+$ PBMC), and optionally RANTES (CCL5), preferably selected from MCSF, IL-3, CCL 18, CCL15, and CCR2 expressed at the surface of PBMC (preferably CCR2 expressed at the surface of CD3$^+$ and/or CD11c$^+$ PBMC), even more preferably selected from at least glycosylated MCSF and CCR2 expressed at the surface of PBMC, preferably together with at least one of IL-3 and CCL18 (PARC), for example together with both IL-3 and CCL18 (PARC), optionally together with anyone of CCL15 (MIP1-delta) and RANTES (CCL5) or with both CCL15 and RANTES. They can also comprise a (bio) marker for normalizing data which can be selected from the group comprising antigen(s) corresponding to circulating range of the selected protein of interest, or to isotype-matched antibody-control to measure the expression of surface markers, etc.

Also herein described is a method for selecting the appropriate anti-inflammatory drug for preventing or treating a cognitive impairment selected from SCI, and MCI, for example eMCI and lMCI, in a subject, wherein the method comprises a step of assessing the cognitive function of the subject using the herein described method.

Preferred molecules to be administered to a subject identified as suffering of SCI or MCI, for example eMCI or lMCI, can be selected from curcumin, a cyclophosphamide, a non-steroidal anti-inflammatory drug (NSAID) such as rofecoxib, and an antibody directed against human IL-12 and IL-23 such as ustekinumab.

Further aspects and advantages of the present invention will be disclosed in the following experimental section, which shall be considered as illustrative only.

LEGENDS TO THE FIGURES

FIG. 1: Methodology for blood separation.

Figure 2:
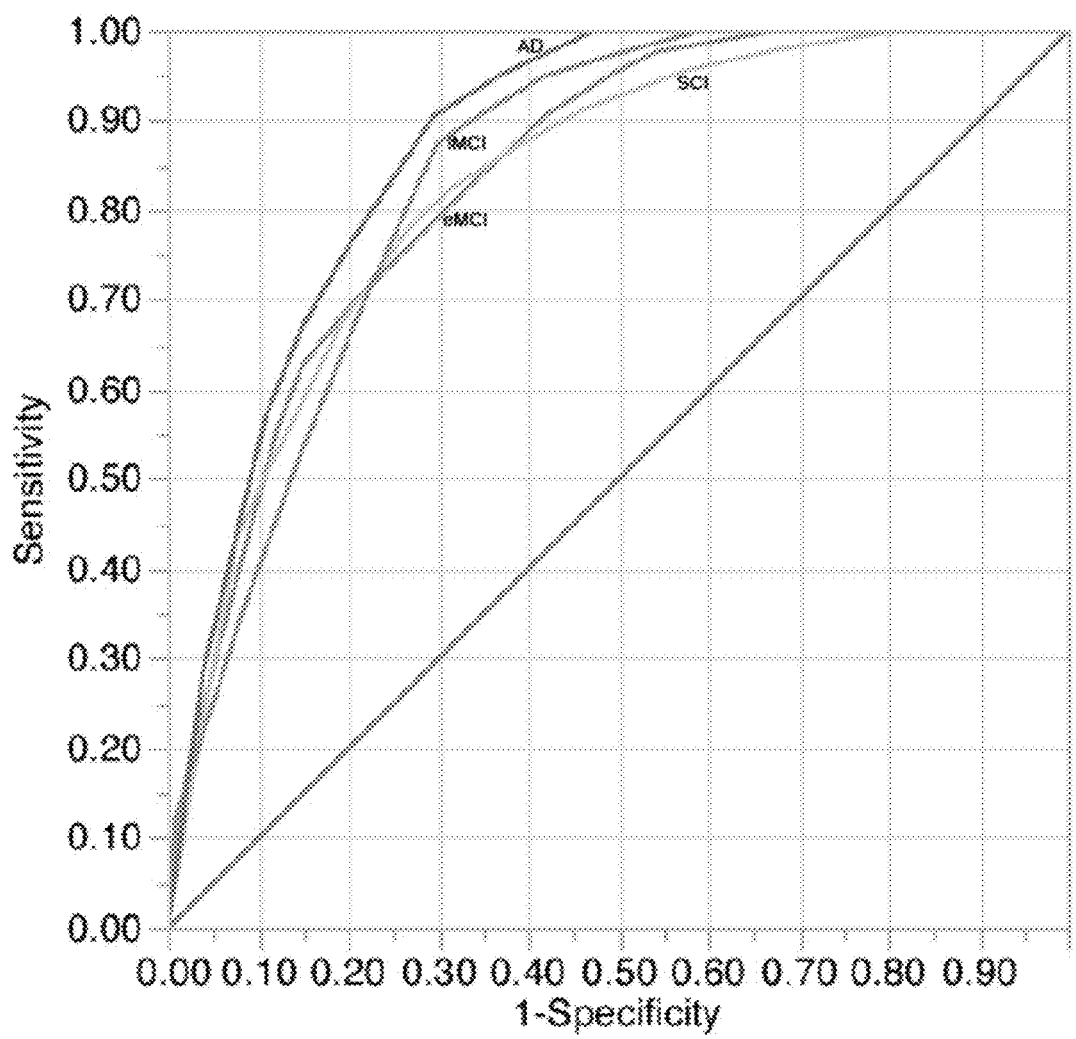

FIG. 2: Example of a Receiver Operating Characteristic curve analysis from one of the retained model. Area under the ROC curve, with standard error and 95% confidence. Each line represents the classification performance for a single group (as labeled).

Figure 3A:
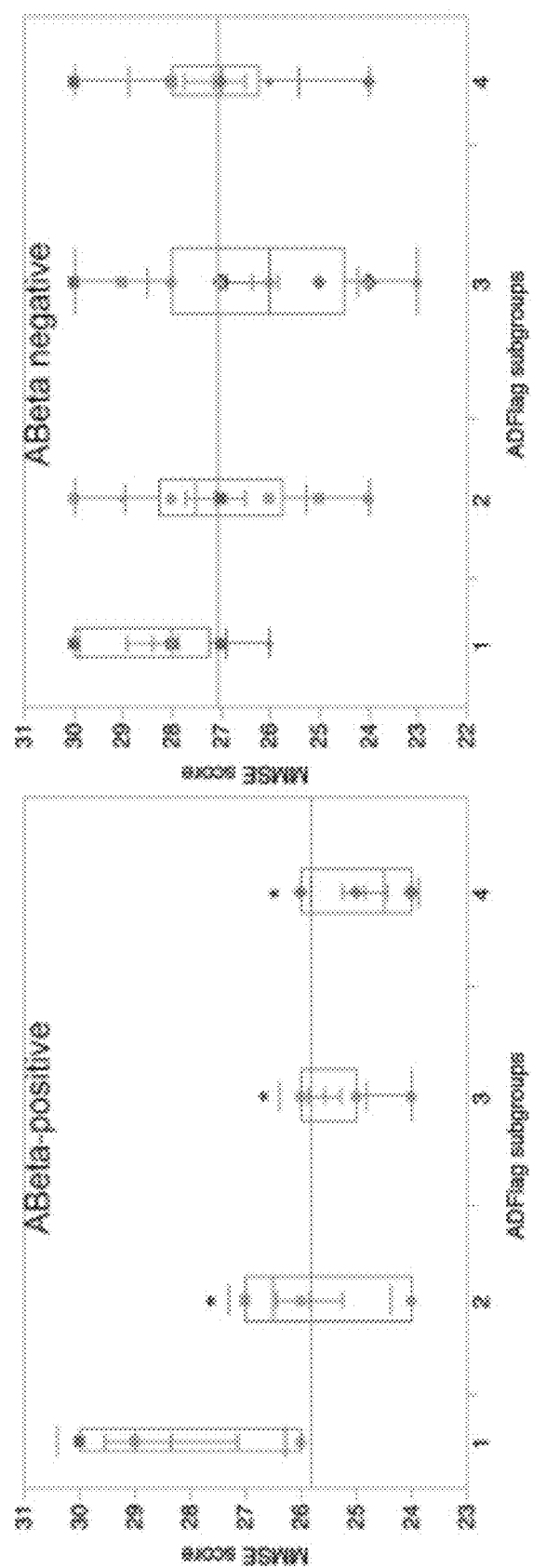
Figure 3B:
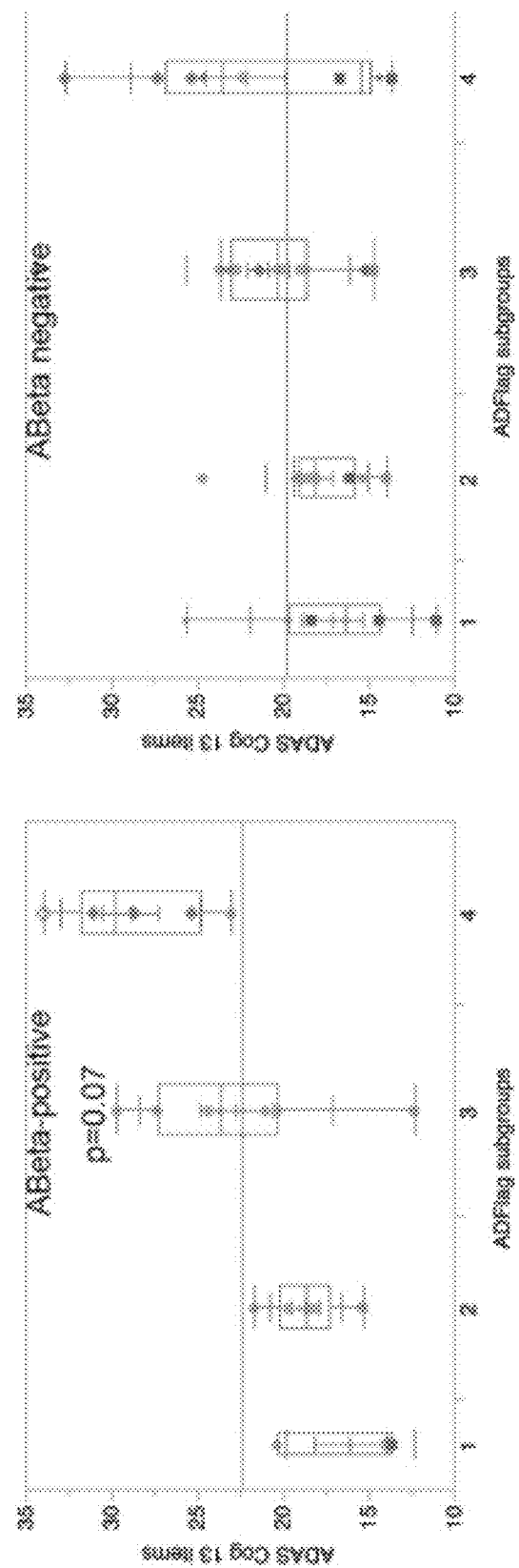

FIGS. 3A-3B: Repartition of the average, standard deviation and quantiles in the different subgroups defined by the described protein panel in Abeta positive and Abeta-negative training sets. FIG. 3A: with respect to MMSE score, FIG. 3B: With respect to ADAS-Cog scores (13 items).

Figure 4A:
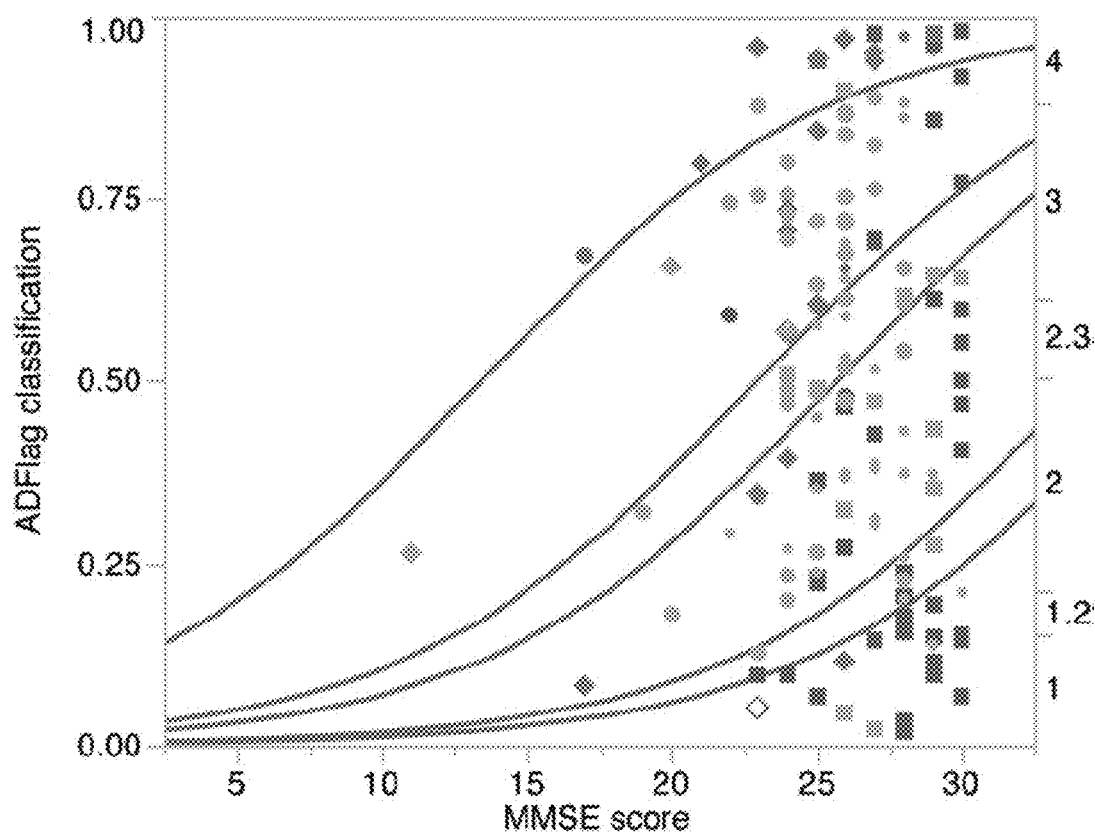
Figure 4B:
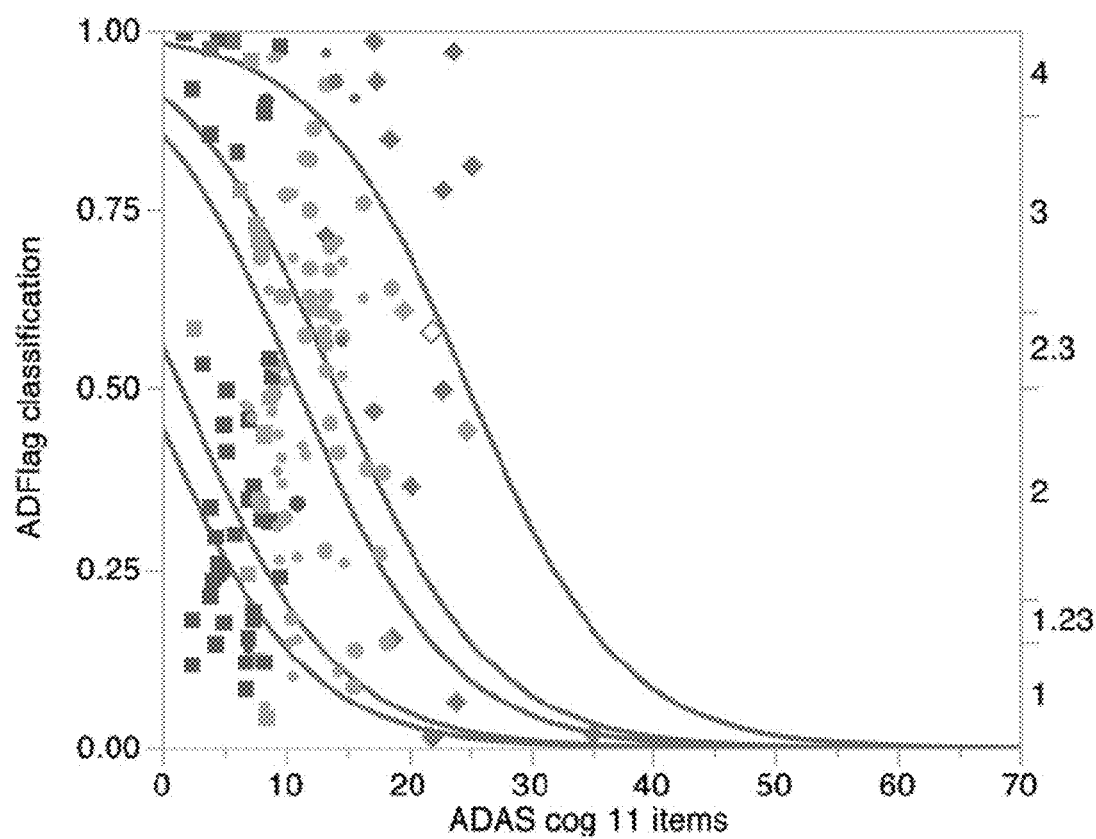
Figure 4C:
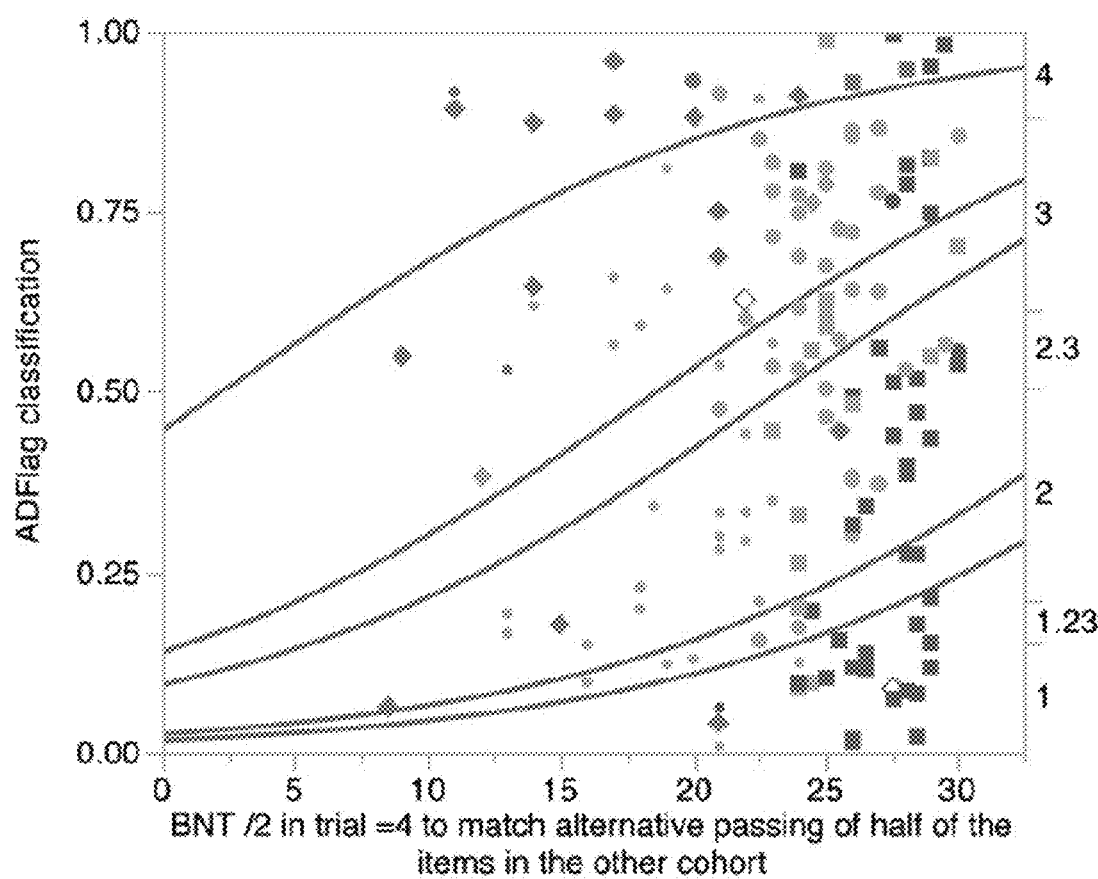

FIGS. 4A-4C: A nominal logistic regression was used to evaluate the potential association of the novel protein classification model herein described and the three neuropsychological scales used in both trial 1 and trial 4 populations. Squares represent SCI patients, circles indicate MCI patients (small circle: early MCI, large circle: late MCI), and diamonds represent AD patients. FIG. 4A: Association with MMSE scores, FIG. 4B: Association with ADAS-Cog scores (11 items), FIG. 4C: association with Boston Naming_test (BNT) standardized scores.

Figure 5:
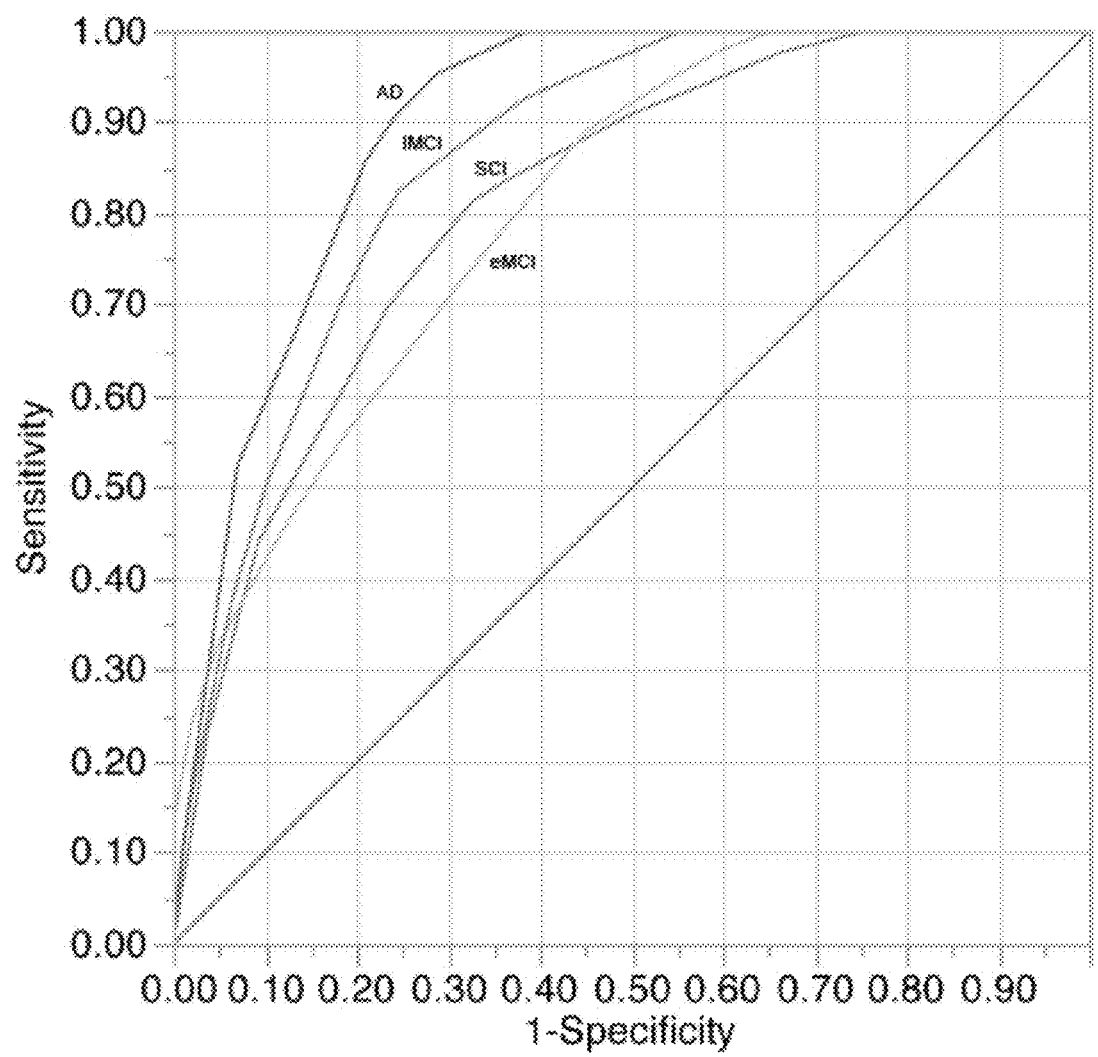

FIG. 5: Area under the ROC curve, with standard error and 95% confidence. Each line represents a subgroup identified by the protein panel profile in whole blood.

Figure 6:

FIG. 6: Markers expression patterns depending on the impairment.

Figure 7:
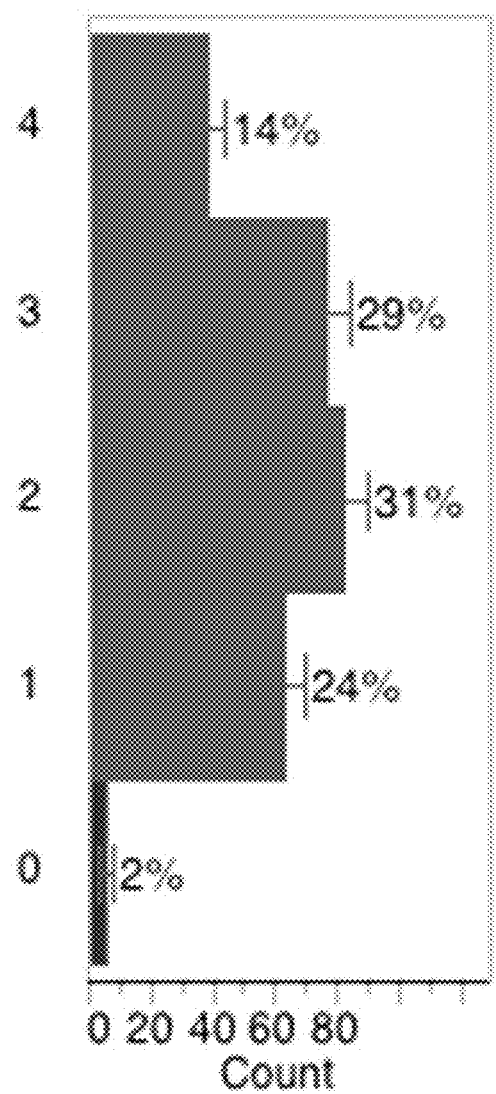

FIG. 7: Histogram distribution of the baseline cross-sectional patients within the different diagnostic classes. 0=normal, 1=SCI, 2=early MCI, 3=late MCI, 4=AD.

Figure 8:
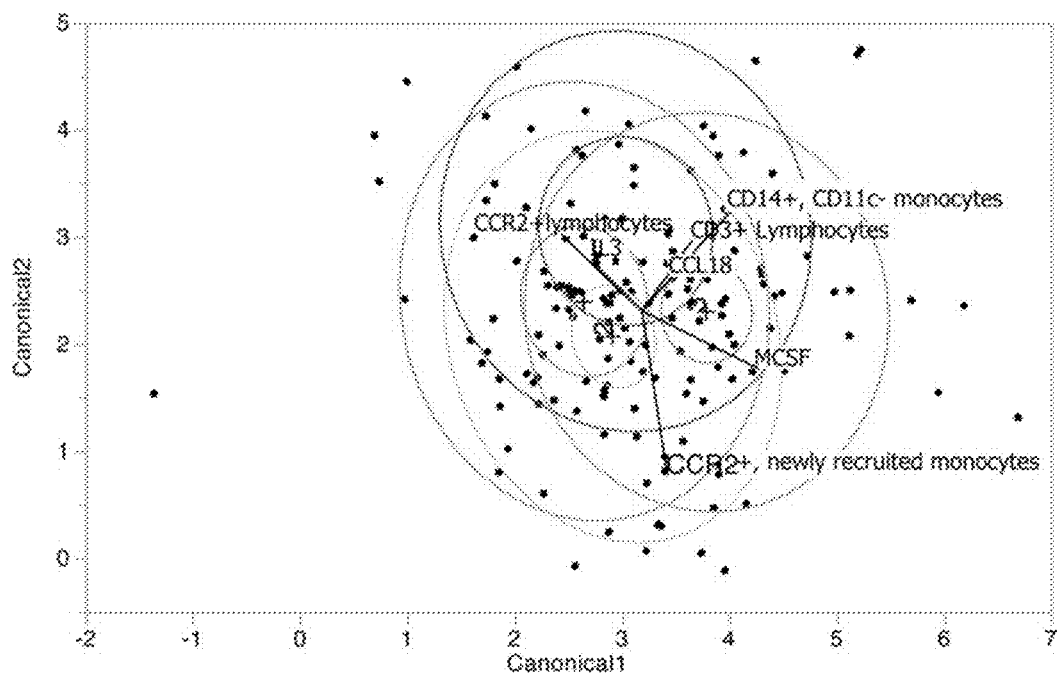

FIG. 8: Regularized discriminant analysis of the patient population identifying variables capable of segregating homogeneous subgroups associated with actual diagnostic scores (1=SCI, 2=early MCI, 3=late MCI, 4=AD).

Figure 9:
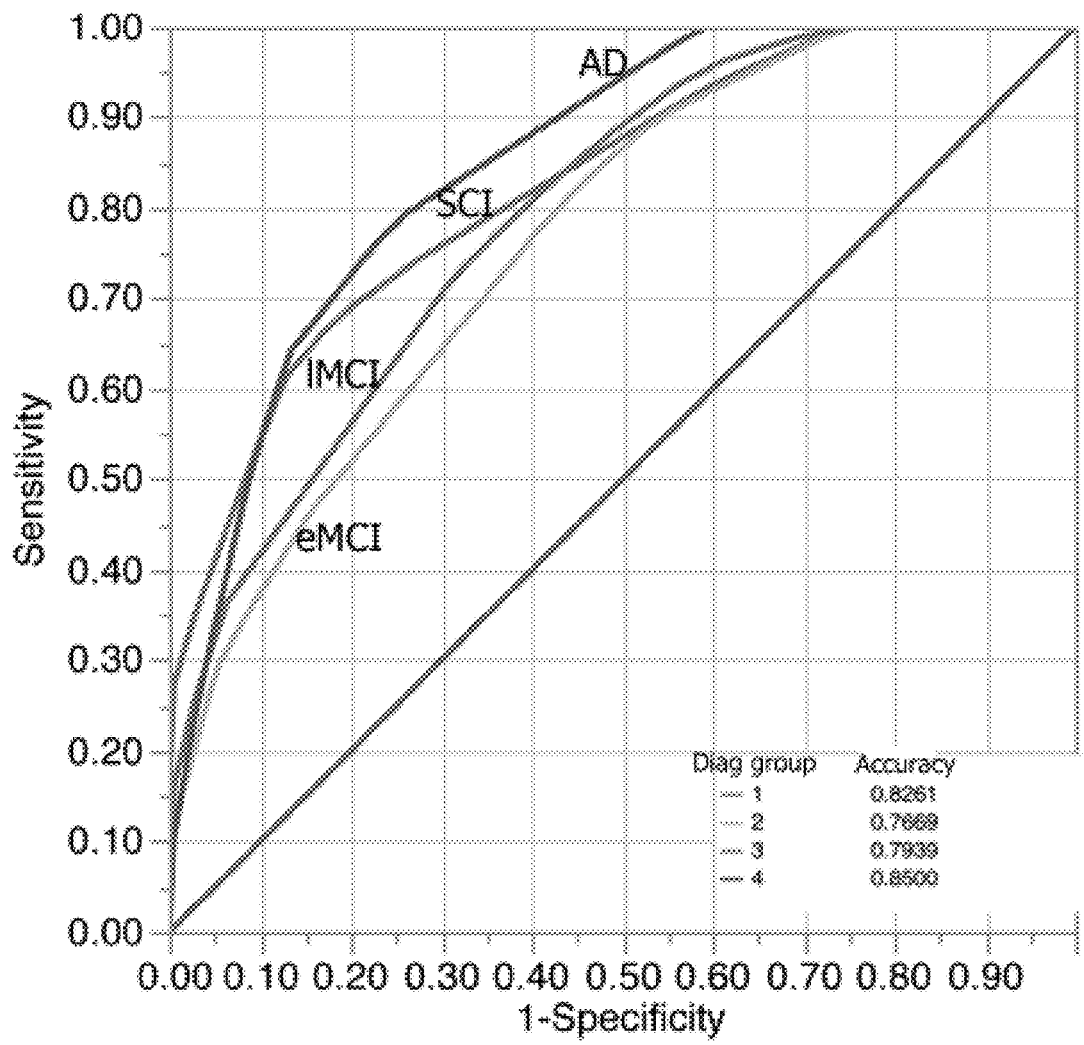

FIG. 9: Receiver Operating Curve (ROC), with standard error and 95% confidence. Each line represents a subgroup identified by the protein panel profile in whole blood in the current patient population (n=268).

Figure 10A:
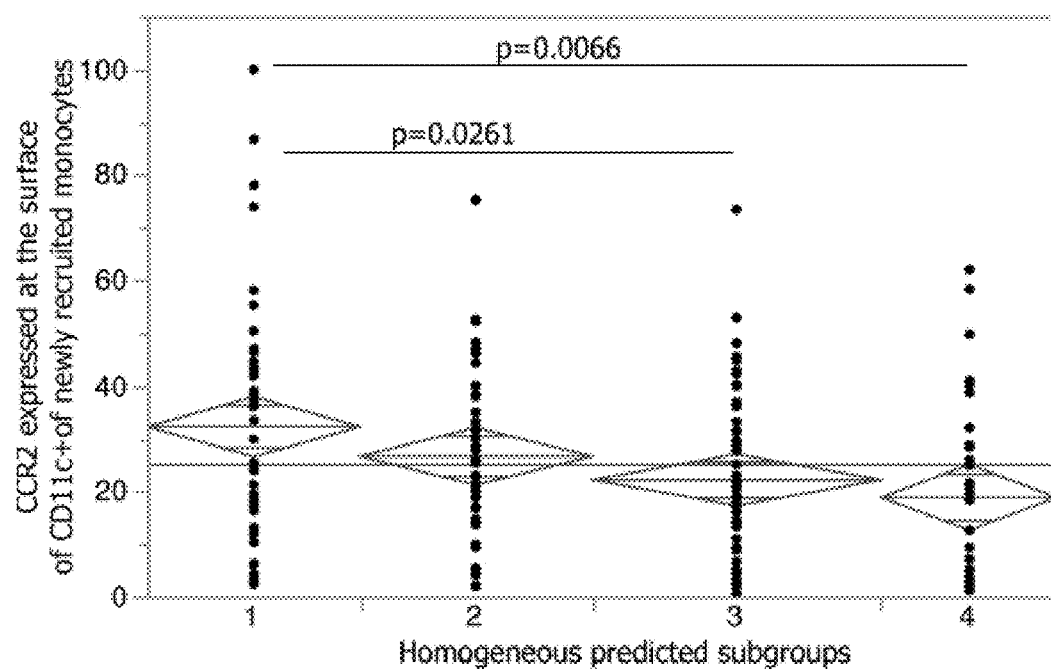
Figure 10B:
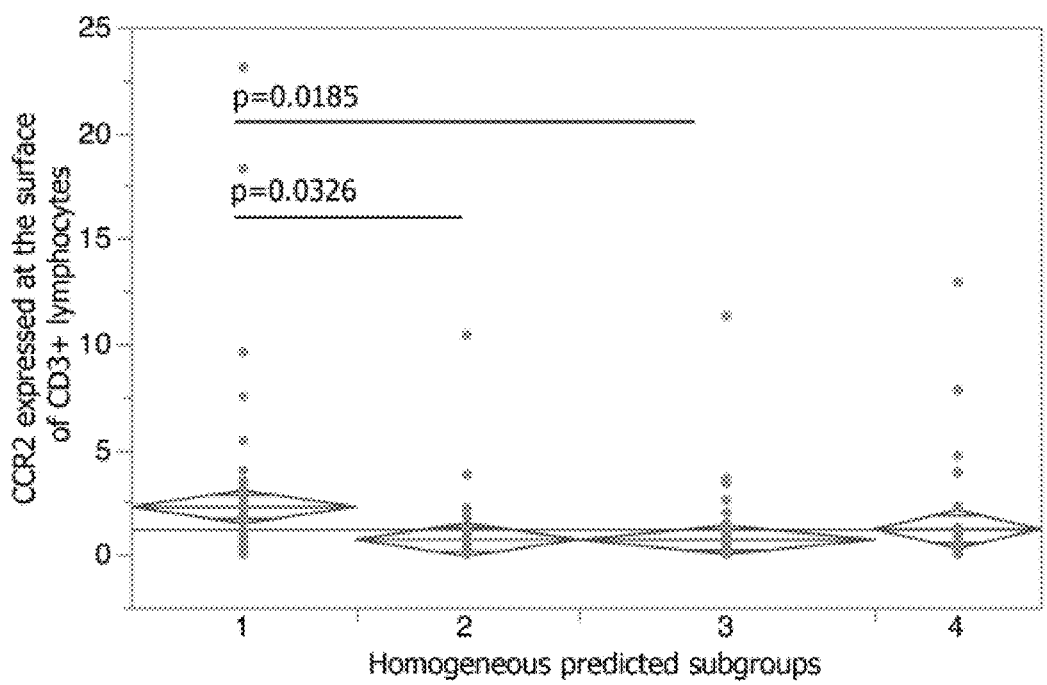

FIGS. 10A-10B: Expression of CCR2 is associated with disease progression. FIG. 10A: At the surface of CD11c$^+$ newly recruited dendritic cells. FIG. 10B: At the surface of CD3$^+$ lymphocyte cells. ANOVA shows significant difference in CCR2 expression in SCI group compared to the over subgroups.

Figure 11:
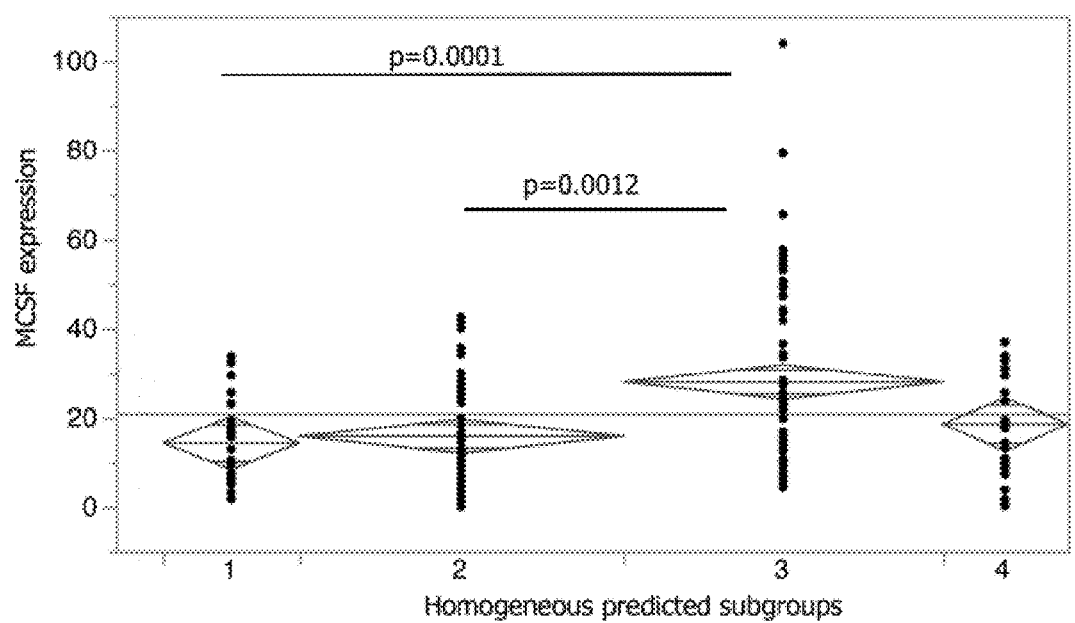

FIG. 11: Expression of MCSF in circulating plasma. ANOVA shows significant difference in MCSF expression in late MCI group compared to the over subgroups and particularly compared to SCI and early MCI subgroups.

Figure 12:
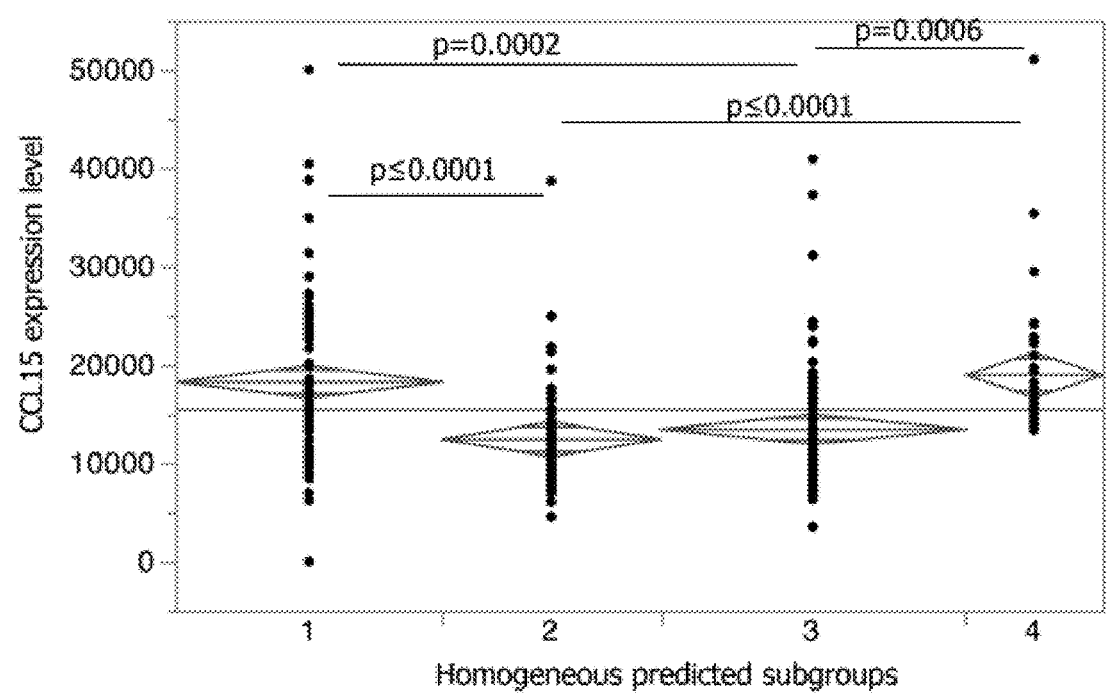

FIG. 12: Expression of CCL15 in circulating plasma. ANOVA shows significant difference in CCL15 expression in early and late MCI groups compared to either SCI or AD subgroups.

Figure 13:
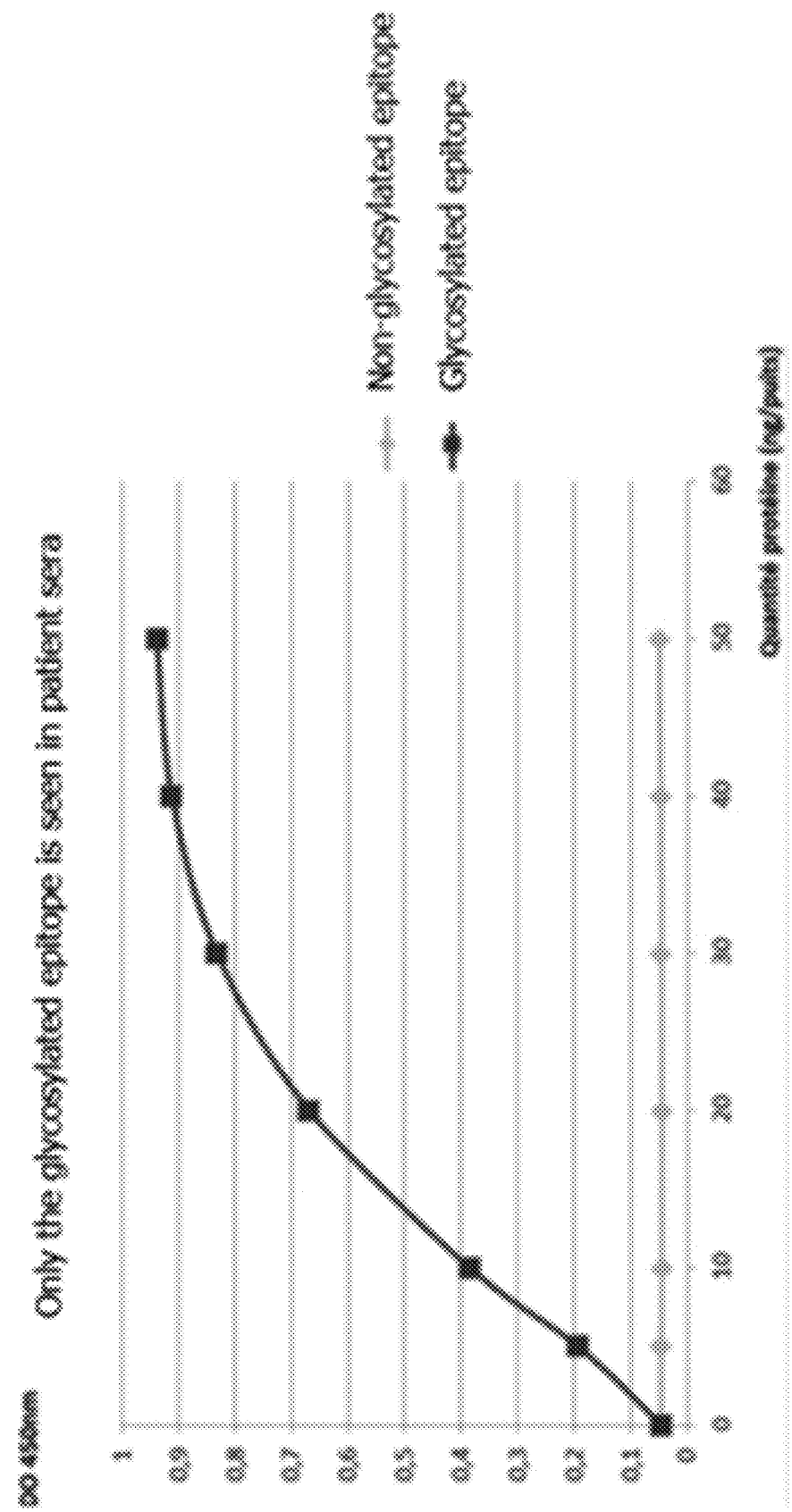

FIG. 13: Epitope mapping of MCSF showing that only glycosylated forms of MCSF (dark grey line, square markers) are recognized by the antibody used in the immunoassay developed. Non-glycosylated epitope are not recognized (light grey line, diamond markers).

Figure 14:
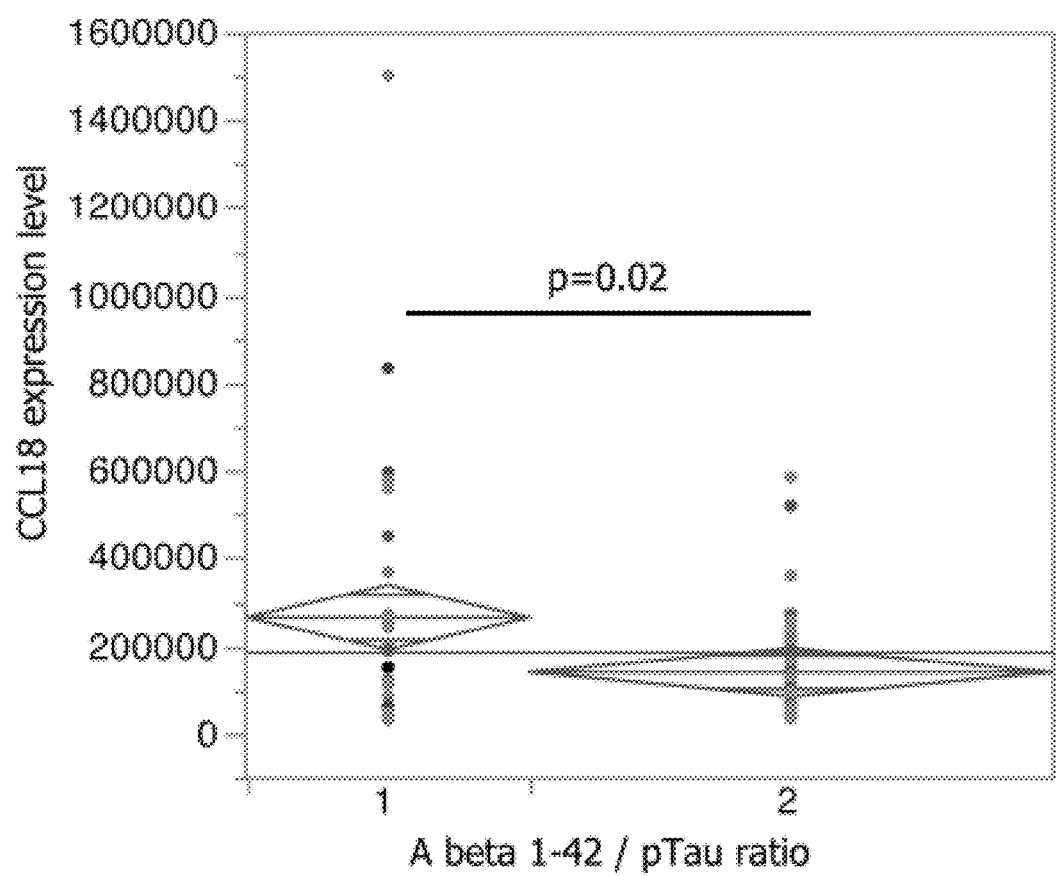

FIG. 14: Expression of CCL18 in patients most at risk to develop AD (as defined by their Amyloid beta 1-42/pTau ratio). Patients with the highest risk to develop AD (ratio ≤8.8, group 2) showed significantly different CCL18 expression level from patients less likely to develop AD (ratio 8.8<Abeta1-42/pTau<15.2, group 1).

Figure 15:
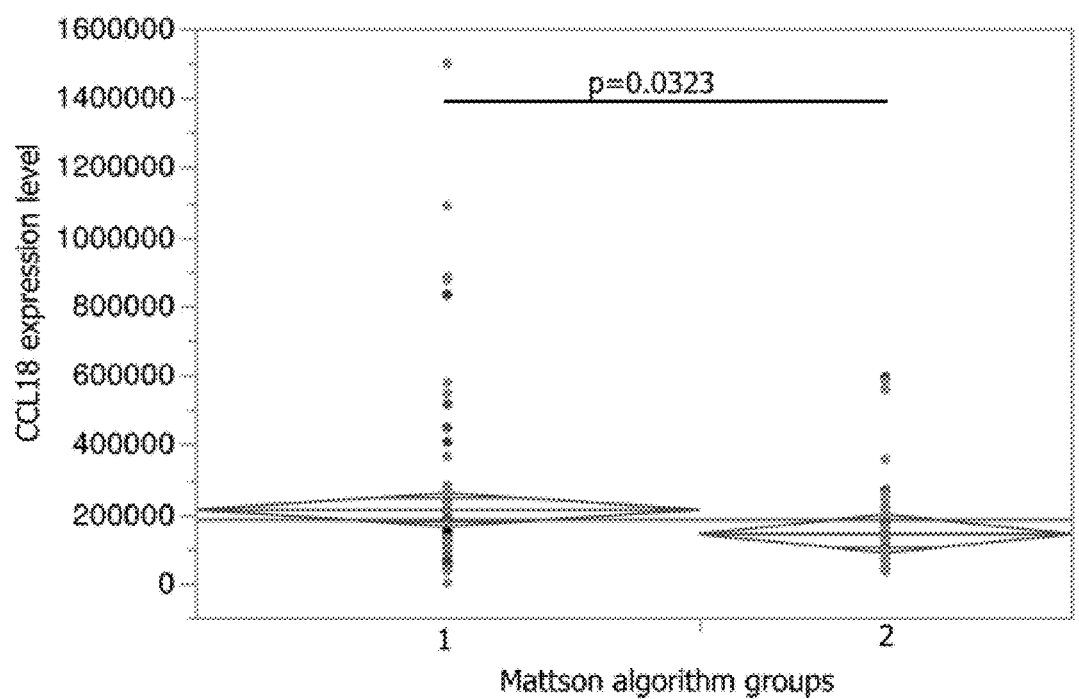

FIG. 15: Expression of CCL18 in patients most at risk to develop AD (as defined by the Mattsson algorithm). Patients with the highest risk to develop AD (Ab42/pTau<3.694+0.0105*t-tau, group 2) showed significantly different CCL18 expression levels from patients less likely to develop AD (Ab42/pTau≥3.694+0.0105*t-tau, group 1).

Figure 16:
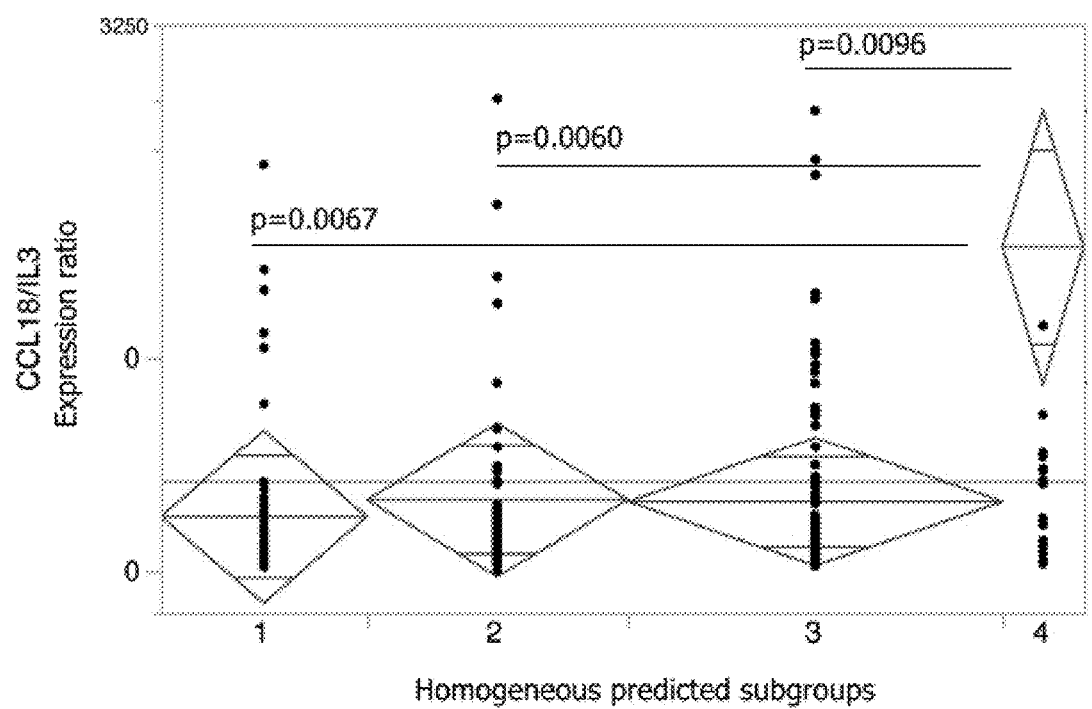

FIG. 16: The ratio of CCL18/IL3 expression levels in circulating plasma. ANOVA shows significant difference in CCL18/IL3 expression Ad group (group 4) compared to all the pre-dementia subgroups (group 1-3).

Figure 17:
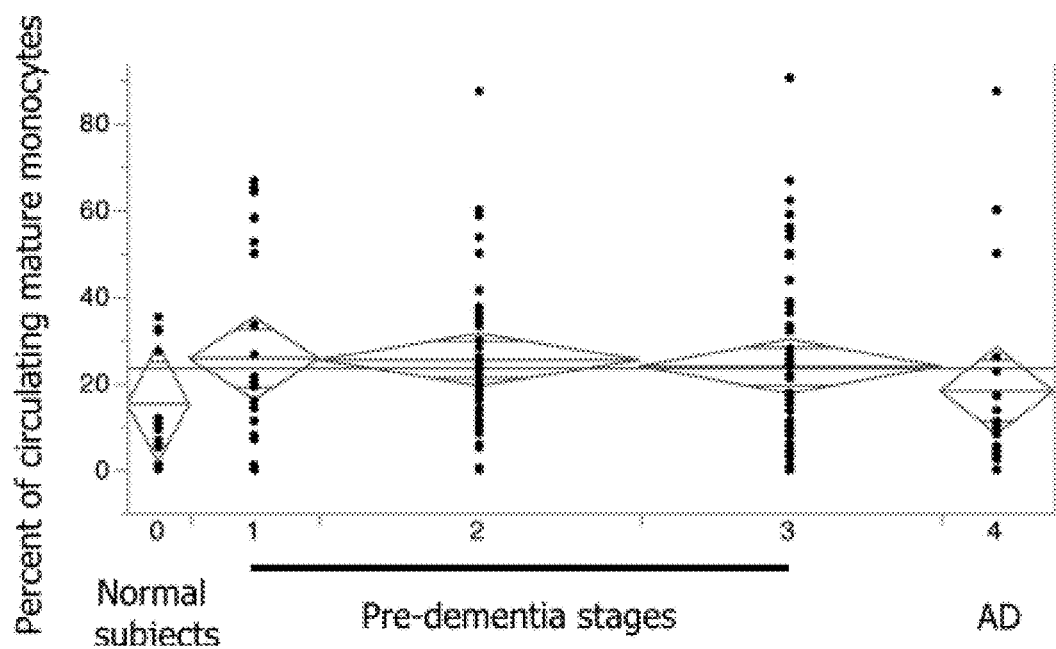

FIG. 17: The level of circulating mature monocytes expressing at least CD11c and low levels of CD14 is representative of the disease state as pre-dementia stages are associated with higher levels of these cells circulating in the blood compared to either normal subjects or subjects with confirmed AD.

EXAMPLES

Example 1

The present example illustrates the utility of the protein set identified to classify patients consulting a memory clinic based on their actual risk of developing Alzheimer's disease, specifying the degree of progression associated with the disease state.

Material and Method

Proteins identified from an approach coupling the cellulomic analysis of mitochondrial behavior in somatic patient-derived cells and the proteomic analysis of differential protein expression in peripheral mononuclear blood cells (PBMC) were measured in blood.

Whole blood was separated (see FIG. 1) into two main compartments using CPT-heparin tubes to separate PBMC from plasma. Plasma was immediately stored at −80° C. and cells were collected into freezing medium. Cells were frozen 1:1 in freezing medium. Vials were labeled with the anonymized tracking number based on trial specification. Vials were placed inside a passive freezer filled with isopropyl alcohol and place at −80° C. overnight. Frozen vials should be transferred to −80° C. storage box with the collected plasma from the same patient until they can be transferred in vapor phase of a liquid nitrogen storage vessel and the location recorded. Blood samples should be centrifuged/separated within two hours of blood drawing.

Proteins present in the plasma compartment (MCSF, IL-3, CCL15, CCL18, RANTES) were measured using multiplexed immunoassays. Briefly specific captured antibodies were coupled to magnetic beads either in multiplex or simplex format. Beads were put in contact with the biological matrix in which the proteins of interest were present. After 1 h incubation, the sample was removed, beads washed and incubated in the presence of a secondary antibody coupled to phycoerythrin. Signal revelation was allowed to occur for 15 minutes prior to sample washing and signal detection. Signal was read on a Magpix X-map reader.

Proteins present in the PBMC compartment were evaluated using fluorescence-activated cell sorting (FACS) measurements. Flow cytometry was performed using a FAC-Scan. The fluorescence of 100000 cells was collected on a 1024-channel four-generation log scale through forward light scatter (FSC) and linear scale through right-angle scatter (SSC). Fluorescence emission for fluorescein was determined at 530 nm (FL1) and the PE emission was determined at 585 nm (FL2). CD3, CD11c and CCR2 expression at the surface of PBMC was measured.

ICDD's biobank is constituted of blood samples collected in two different trials, analyzed in a cross-sectional manner to identify pre-symptomatic stages of AD. In example 1 the results from the "trial 4" cohort (n=170), a mono-centric sampling, are presented. In example 2, the results from the "trial 1" cohort (n=147), a multi-centric sampling in 14 European centers, are presented.

In this first example, inventors' goal was to test whether the combined expression of several proteins defines expression patterns co-segregating with the clinical expression of cognitive loss in patients likely to develop Alzheimer's disease.

The "trial 4" cohort was used to evaluate the performances of the protein panel to segregate patients based on Alzheimer's disease progression.

Results

The trial 4 cohort was sufficiently large to encompass all categories of patients, i.e. patients suffering of any presymptomatic impairment or AD. The different groups were significantly different in their MMSE scores ($p<0.0001$) except for eMCI and lMCI group. Note that the MMSE scores were considered below the disease threshold in all the presymptomatic groups. All groups were also different in their ADAS-Cog scores ($p<0.0001$) and significantly distinct one from another. Similarly, the BNT scale also discriminated SCI patients from the group of MCI patients and from AD patients. The different patients enrolled were within the same age group. However, the lMCI group was significantly older than the SCI group ($p=0.02$). Women were more represented than men in the whole cohort. Surprisingly, the highest frequency of women in the cohort was not only seen in AD-patient group, but also in SCI patients. The late MCI group resented a significantly lower education level than the other groups and particularly than the SCI group. Hence, age, education level and gender could represent co-funding co-factors.

TABLE 1

Baseline characteristics

| | Trial 4 | | | |
|---|---|---|---|---|
| | SCI (n = 47) | eMCI (n = 32) | lMCI (n = 12) | AD (n = 6) |
| Age (year) | 71.67 +/− 9.62 | 73.58 +/− 5.69 | 79.08 +/− 3.70 | 79.11 +/− 7.37 |
| Year in educ. | 4.83 +/− 1.86 | 3.65 +/− 1.80 | 2.83 +/− 1.64 | 3.55 +/− 1.74 |
| Women | 64.00% (32) | 54.55% (18) | 50.00% (6) | 77.78% (7) |
| MMSE | 28.29 +/− 1.80 | 25.56 +/− 2.69 | 23.63 +/− 2.77 | 15.78 +/− 6.26 |
| ADAS-cog | 5.24 +/− 2.11 | 8.03 +/− 2.04 | 11.05 +/− 2.89 | 30.67 +/− 12.24 |
| BNT | 27.38 +/− 2.00 | 24.42 +/− 3.05 | 21.46 +/− 5.47 | 19.25 +/− 7.95 |
| Carrier APO e4 | 24.14% (7) | 13.05% (3) | 50.00% (6) | 44.44% (4) |
| Blood Ab$_{42/40}$ (pg/ml) | 0.35 +/− 0.43 | 0.25 +/− 0.03 | 0.26 +/− 0.04 | 0.25 +/− 0.06 |

Data are mean (SD) or number (%). Data are uncorrected. MMSE=mini-mental state examination. ADAS-Cog=Alzheimer's Disease Assessment Scale—Cognitive, BNT=Boston Naming test. APOE=apolipoprotein E. Aβ42=β-amyloid 1-42. T-tau=total tau. P-tau=phosphorylated tau.

SCI=subjective cognitive impairment, eMCI=early mild cognitive impairment, lMCI=late mild cognitive impairment AD=Alzheimer's disease. Threshold concentrations of Aβ42 was 550 pg/mL and concentrations of T-tau were 759 pg/mL (data from patients analysed in the same laboratory that did the analysis in the present study).

The protein panel selected provided a classification that separated four different homogeneous groups solely on the basis of protein expression profiling. They were derived from a decision tree algorithm that segregated the four groups in successive steps of pruning Several different models were kept with similar performances as seen in table 2 below. An original training set of 58 patients was tested using blood samples from different patients than those used for the discovery of the protein panel. Retrospective analysis of the performances of this model when compared to actual diagnostic based on neuropsychological examination and medical image analysis is shown on FIG. 2 [Data are area under the curve of a receiver operating characteristic curve (ROC)].

TABLE 2

Partition models used to identify the different subgroups based on protein expression profile

|  | Model1 (n = 58) | Model2 (n = 81) | Model 3 (n = 81) | Segregating proteins |
|---|---|---|---|---|
| SCI | 0.76 | 0.84 | 0.84 | CD3, MCSF, IL3, CCL18 |
| eMCI | 0.82 | 0.83 | 0.78 | MCSF, CCL15, CCR2 |
| lMCI | 0.83 | 0.84 | 0.84 | CD11c, MCSF, CCL15, CCL18, RANTES, CCR2 |
| AD | 0.90 | 0.87 | 0.92 | MCSF, CCL18, CCR2, CD3, RANTES, IL3 |

With these performances, patients were grouped in 4 biological homogeneous subsets. Their characteristics are described in the table 3 below.

TABLE 3

Classified training set characteristics.

| | Biologically classified groups | | | | |
|---|---|---|---|---|---|
| | SCI (n = 13) | eMCI (n = 25) | lMCI (n = 10) | AD (n = 9) | p |
| Age (year) | 73.08 +/− 9.21 | 73.97 +/− 6.42 | 75.26 +/− 5.51 | 73.33 +/− 13.61 | NS (p = 0.988) |
| MMSE | 27.85 +/− 1.77 | 25.32 +/− 2.83 | 23.52 +/− 5.59 | 25.50 +/− 4.08 | p = 0.018 (*) |
| ADAS-cog | 5.54 +/− 1.89 | 9.51 +/− 6.12 | 10.61 +/− 4.56 | 9.13 +/− 5.82 | p = 0.081 |
| BNT | 26.85 +/− 2.37 | 24.64 +/− 3.90 | 25.26 +/− 4.27 | 22.75 +/− 5.715 | NS (p = 0.295) |
| Blood Ab$_{42/40}$ (pg/ml) | 0.23 +/− 0.04 | 0.25 +/− 0.03 | 0.28 +/− 0.04 | 0.28 +/− 0.05 | p = 0.050 |

Table 3 shows that the biological classification obtained differs from the diagnostic group characteristics only in the AD group. AD patients in this group, randomly selected, were young, with a high cognitive functioning despite being clinically recognized as affected by the disease, likely impacting the results in this small training set. Results showed that the 3 presymptomatic subgroups segregated as expected in the MMSE scale (p=0.018), in the ADAS-Cog scale (p=0.081) and in the BNT scale. The evolution of the circulating Amyloid beta 40/42 ratio increased with increasing cognitive impairment.

To confirm these results, the analysis was prospectively extended to a larger population within the same cohort and to a second cohort including more MCI patients, to ascertain the capability of biologically separating early from late MCI. Results are shown in example 2.

Example 2

Example 1 shows the initial biological validation of the protein panel described in the present invention. Example 2 demonstrates that this same protein panel is capable of segregating early from late MCI. Cross sectional study at baseline served this objective in example 2.

The cross sectional study used counted 147 enrolled patients, from 14 investigation centers across Europe. A total of 139 patients completed all neuropsychological testing and were used to prospectively validate the protein panel identified in the present invention. Table 4 describes the baseline characteristics of the patients who provided the blood samples.

TABLE 4

Baseline characteristics of the validation cohort prospectively classified using the circulating biological markers

| | Trial 1 (n = 139) | | | |
|---|---|---|---|---|
| | SCI (n = 28) | eMCI (n = 53) | lMCI (n = 47) | AD (n = 10) |
| Age (year) | 64.96 +/− 8.01 | 69.57 +/− 7.49 | 70.55 +/− 5.79 | 72.20 +/− 7.67 |
| Year in educ | 4.82 +/− 1.91 | 3.96 +/− 2.24 | 3.02 +/− 2.31 | 3.1 +/− 2.42 |
| Women | 22.97% (17) | 49.06% (n = 26) | 57.45% (n = 27) | 40% (n = 4) |
| MMSE | 28.32 +/− 1.95 | 26.32 +/− 1.61 | 25.82 +/− 1.36 | 26.00 +/− 2.00 |
| ADAS-cog | 7.31 +/− 1.84 | 11.20 +/− 2.94 | 15.96 +/− 3.72 | 24.73 +/− 8.42 |
| BNT | 26.07 +/− 2.65 | 23.04 +/− 4.00 | 20.36 +/− 4.25 | 13.20 +/− 6.96 |
| Carrier APO e4 | 57.14% (n = 16) | 35.29% (n = 18) | 46.81(n = 22) | 50% (n = 5) |
| CSF Ab42 (pg/ml) | 774.3 +/− 233.0 | 699.8 +/− 342.7 | 659.5 +/− 267.8 | 442.7 +/− 114.7 |
| CSF T-tau (pg/ml) | 285.2 +/− 233.3 | 479.1 +/− 360.7 | 563.4 +/− 275.7 | 721.3 +/− 588.0 |
| CSF p-Tau (pg/ml) | 48.78 +/− 27.43 | 68.54 +/− 36.44 | 78.59 +/− 42.18 | 97.33 +/− 66.89 |

Data are mean (SD) or number (%). Data are uncorrected. MMSE=mini-mental state examination. ADAS-Cog=Alzheimer's Disease Assessment Scale—Cognitive, BNT=Boston Naming test. APOE=apolipoprotein E. Aβ=β-amyloid 1-42. T-tau=total tau. P-tau=phosphorylated tau.

SCI=subjective cognitive impairment, eMCI=early mild cognitive impairment, lMCI=late mild cognitive impairment AD=Alzheimer's disease. Threshold concentrations of Aβ42 was 550 pg/mL and concentrations of T-tau were 759 pg/mL (data from patients analysed in the same laboratory that did the analysis in the present study).

The protein panel described in the present invention segregated Trial 1 patient population in 4 homogeneous subgroups that consisted in three pre-symptomatic patient groups and in 1 group having AD dementia.

Within this cohort a small subset of the patient population (n=65) was used to train the model to recognize the new clinical situation at hand. The patient training set consisted in patients for whom inventors had access to neuropsychological assessment, Amyloid beta CSF measurements as well as a qualitative assessment of presence or absence of hippocampal atrophy. Amyloid beta CSF level, Tau and phospho-Tau CSF level, presence or absence of hippocampal atrophy were shared for only randomly chosen patients. Inventors also tested for an eventual association between the biological classification obtained with the present invention and commercially recognized markers such as Amyloid beta CSF circulating level used as a threshold marker to identify patients most likely to develop AD.

TABLE 5

Characteristics of the training set compared to the entire population

| Cognition, function, imaging and CSF markers | Whole Phamacog T0 cohort (n = 142) | CSF-positive (n = 22) Below 550 | CSF-negative (n = 43) Above 550 | p |
|---|---|---|---|---|
| Mini Mental State Examination | 26.6 ± 1.8 | 25.82 +/− 1.59 | 27.05 +/− 1.97 | 0.01 |
| ADAS-COG | 20.34 +/− 6.57 | 22.35 +/− 1.16 | 19.73 +/− 0.86 | 0.07 |
| Spatial working memory | 43.6 ± 21.7 | 48.68 +/− 22.0 | 45.62 +/− 22.1 | .625 |
| Occurence of Hippocampal atrophy Lx | 23.47% | 13.85% | 21.54% | .507 |
| Occurence of Hippocampal atrophy Rx | 15.31% | 7.69% | 15.38% | 0.962 |
| A beta-42 (n = 65) | 690.40 +/−292.63 | 399.13 ± 81.48 | 839.37 ± 244.97 | .000 |
| Tau (n = 65) | 477.06 +/− 333.24 | 603.5 +/− 445.3 | 412.4 +/− 239.5 | .027 |
| pTau | 69.01 +/− 39.42 | 86.54 ± 50.58 | 60.05 ± 29.07 | .009 |

Similarly to what was previously shown in example 1, the biologic classification presented in the invention generated 4 subgroups related to disease progression, three being pre-symptomatic and one being associated to a high probability to develop AD. Table 6 summarizes the characteristics of the 4 different subgroups generated by the ADFlag assay (partial preliminary analysis):

|  | SCI (n = 9) | early MCI (n = 27) | late MCI (n = 46) | AD (n = 8) |
| --- | --- | --- | --- | --- |
| Demographics (n = 90 training set) |  |  |  |  |
| Age | 67.88 +/− 7.64 | 69.22 +/− 8.63 | 69.73 +/− 7.12 | 70.37 +/− 7.56 |
| Gender | 55.56% fem | 44.44% fem | 60.87% fem | 75.00% fem |
| Cognition, function, imaging and CSF markers |  |  |  |  |
| Mini Mental State Examination | 28.22 +/− 1.48 | 27.55 +/− 1.67 | 25.73 +/− 1.48 | 26.62 +/− 2.62 |
| ADAS-COG | 16.87 +/− 1.74 | 16.83 +/− 4.87 | 21.84 +/− 6.90 | 23.91 +/− 8.15 |
| BNT | 24.44 +/− 2.35 | 22.74 +/− 4.98 | 22.87 +/− 4.46 | 18.75 +/− 5.95 |
| Occurrence of Hippocampal atrophy Lx | 20.0% | 20% | 39.39% | 62.5% |
| Occurrence of Hippocampal atrophy Rx | 0% | 5% | 27.27% | 62.5% |
| A beta-42 (n = 65) | 709.4 +/− 128.5 | 644.9 +/− 334.1 | 714.4 +/− 320.9 | 687.5 +/− 191.0 |
| Tau (n = 65) | 367.2 +/− 383.8 | 447.3 +/− 424.3 | 496.0 +/− 267.1 | 538.75 +/− 372.9 |
| pTau | 57.6 +/− 42.0 | 64.3 ± 36.7 | 72.0 ± 40.6 | 71.6 +/− 41.2 |

On the demographic characteristics, the 4 different subgroups defined by the biological classification described in the present invention did not significantly differ. Despite gender being more unbalanced with disease progression in the 4 diagnostic subgroups, this effect was not significant in the training set. It may be retained as a cofounding co-variant in further analyses.

It was interesting to observe that a clear increase in the frequency of the occurrence of hippocampal atrophy accompanied the disease progression as assessed by the biological classification using the novel protein panel herein described. This effect was seen both from the right and the left hemisphere.

The cognitive scales examined were limited to the MMSE, ADAS-Cog and BNT (scales also present in our initial study in a more diverse population). With the ADFlag panel, SCI, early MCI and late MCI subgroups significantly differ on the MMSE scale (p<0.0001). The early and late MCI groups differ from the most likely AD group on the ADAS-COG scale (p=0.0105). Finally, the SCI and most likely AD groups were segregated by the BNT scale (NS, p=0.07).

If CSF beta amyloid level was not significantly different in the trial 1 training subset used, it was differentially expressed in the Abeta-positive population, in which the 4 different subgroups were significantly different in the MMSE scale (p=0.0079) and in the ADAS-Cog scale (p=0.001) not seen in the Abeta-negative scale (see FIG. 3).

Inventors then extended the study to the whole trial 1 population (n=139). Patients were prospectively classified using the protein model defined earlier. The evaluation of the accuracy of the classification obtained with the novel protein panel was evaluated using a nominal logistic regression (see FIG. 4). Inventors confirmed a significant association between the novel protein classification and both the MMSE and the ADASCog scales. This was also true with the BNT scale.

These results show a clear and significant association of the classification obtained with the three neuropsychological scales used to establish the clinical diagnosis of AD. A progressive reduction of both MMSE and BNT scores accompany the classification of patients in group 1-4, group 1 being the least affected by disease progression while group 4 is very likely to develop AD. Inversely, the ADSCog scale scores progresses with the classification 1-4 demonstrating the worsening of cognitive function in the different subgroups identified with the novel protein panel classification.

The classification performances of the protein panel described in the present example using trial 1 cohort are shown in the FIG. 4. The ROC curve depicted shows the ability of the blood protein panel to segregate the SCI, eMCI, lMCI and most likely AD group with 72-88% precision (see ROC curve FIG. 5). The area under the curve (AUC) was 0.73 for SCI, 0.79 for eMCI, 0.83 for lMCI and 0.87 for most-likely AD. These performances were similar to those previously seen with the same panel in a more diverse cohort containing a larger progression of AD.

Example 3

Inventors further sought to identify the discriminant power of specific proteins for the diagnostic stages to segregate. The analysis was done on a multi-cohort, multi-centric dataset grouping 311 patients screened at baseline. Distribution of the Patient Population into the Different Classes of Diagnostic:

Few patients enrolled were considered as normal (class 0). They were analyzed to identify any potential circulating marker capable of discriminating this population from the rest of the patients all considered to bear potential risk of developing a dementia. However, due to the low number of the "normal" patient population these individuals were then removed from the dataset. SCI, early MCI and late MCI patients were balanced within the sample. See histogram repartition based on baseline diagnostic of the patients (class 1—24%), early MCI (class 2—31%), late MCI (class 3-29%) and AD (class 4—14%) (cf. FIG. 7).

The normal population was initially discriminated through PBMC cell sorting, patients at a pre-dementia stage of the disease and AD patients being characterized by an increase in the proportion of circulating mature monocytes as shown in FIG. 17. Mature monocytes are positive for CD11b, CD11c, CD13, CD14, CD33, and CD64, and may express CD2 and CD4.

A discriminant analysis indicated that pre-dementia stages of AD could be segregated in 3 patient populations based on the expression of CCR2 at the surface of CD3$^+$ lymphocytes, newly recruited dendritic cells and in immature CD14$^+$, Cd11c$^-$ monocytes. IL3, CCL18 and M-CSF expression level in the plasma compartment complemented cell surface expression markers. The cross tab showing the distribution of actual versus predicted categorization of patients in pre-dementia subgroups (1-3) and AD patients was accurate in MCI subgroups (61% for late MCI and 49% for early MCI). 82% of overall MCI patients were properly classified. Similarly, patients diagnosed with AD were accurately classified at 53% (FIG. 8).

Extending the previous analysis to the new patient population set, inventors observed similar performances as those seen in the training set. The ROC curve is shown in the FIG. 9. It indicates that the pre-dementia subgroups (1-3) are recognized with an average of 79% accuracy, similar to the performances seen in the training set. The AD subgroup was recognized with 85% accuracy. These experiments pointed to proteins, which expression was most strongly associated with the different subgroups. SCI subgroup classification largely depended on CCR2 (cf. FIG. 10 A); and to a lesser degree to CCL18 and glycosylated MCSF, but also to CCL15 (cf. FIG. 12). MCI subgroups, particularly late MCI subgroup classification largely depends on glycosylated MCSF expression (cf. FIG. 11) but also on CCR2 expression at the surface of several lymphocytes and monocytes subtype (FIG. 10 B). IL3 expression can further be assessed to identify MCI subgroups, particularly late MCI subgroup.

Less discriminating markers such as CCL15 and RANTES also have segregating capabilities as illustrated in ANOVA results showing that the expression level of CCL15 was significantly different in MCI subgroups compared to either SCI or AD subgroups (cf. FIG. 12).

Regarding expression of MCSF, epitope-mapping studies demonstrated that only glycosylated forms of MCSF were measured since non-glycosylated forms failed to give a signal (cf. FIG. 13). This result may explain discrepancies with the state of the art, in which MCSF expression increases in AD compared to MCI stages, while inventors observed a linear progression of MCSF expression from SCI to early MCI and to late MCI but a decrease in AD population. Knowing that inventors are uniquely measuring glycosylated forms of MCSF, this discrepancy suggests that glycosylation of MCSF may be reduced in AD.

Amyloid beta and Tau/pTau are considered gold-standard markers of AD. Inventors' experiments demonstrated that CCL18 expression level is significantly different in the patient population most at risk to develop AD as defined by the Amyloid beta 1-42/Phospho-Tau ratio (cf. FIG. 14) and by the Mattsson algorithm (cf. FIG. 15).

In inventors' experiments, CCL18/IL3 ratio further segregated the homogeneous subgroup predicted to be associated with AD (cf. FIG. 16).

REFERENCES

Bonin-Guillaume S, Zekry D, Giacobini E, Gold G, Michel J P. Impact économique de la démence (Presse Médicale. 2005; 34(1):35-41)
Brookmeyer R, Johnson E, Ziegler-Graham K, Arrighi H M. *Forecasting the global burden of Alzheimer's disease*. Alzheimer's & Dementia. 2007
Chen, Z., et al. *Methodology and Application of Adaptive and Sequential Approaches in Contemporary Clinical Trials*. Vol. 2012.2012.20.
Chong M S, Sahadevan S. *Preclinical Alzheimer's disease: diagnosis and prediction of progression*. Lancet Neurology. 1 Sep. 2005 [Retrieved 7 Apr. 2014]; 4(9):576-9.
De Meyer G, Shapiro F, Vanderstichele H, Vanmechelen E, Engelborghs S, De Deyn P P, Coart E, Hansson O, Minthon L, Zetterberg H, Blennow K, Shaw L, Trojanowski J Q. *Diagnosis-Independent Alzheimer Disease Biomarker Signature in Cognitively Normal Elderly People*. Archives of Neurology. 2010; 67(8):949-56.
Förstl H, Kurz A. *Clinical Features of Alzheimer's Disease*. European Archives of Psychiatry and Clinical Neuroscience. 1999; 249(6):288-290.
Grundman M, Petersen R C, Ferris S H, et al. (2004). "*Mild cognitive impairment can be distinguished from Alzheimer disease and normal aging for clinical trials*". Arch. Neurol. 61 (1): 59-66.
Henriksen, K., et al., *The future of blood-based biomarkers for Alzheimer's disease*. Alzheimers Dement, 2014. 10(1): p. 115-31.
Inouye, S. K., Foreman, M. D., Mion, L. C., Katz, K. H., & Cooney, L. M., Jr. (2001). *Nurses' recognition of delirium and its symptoms: Comparison of nurse and researcher ratings*. Archives of Internal Medicine, 161, 2467-2473. Evidence Level IV: Nonexperimental Study.
Laske C. el al.: "*Macrophage colony-stimulating factor (M-CSF) in plasma and CSF of patients with mild cognitive impairment and Alzheimer's disease*", Curr. Alzheimer Res., vol. 7, no. 5, August 2010, pages 409-414.
Marksteiner J, Hinterhuber H, Humpel C. *Cerebrospinal Fluid Biomarkers for Diagnosis of Alzheimer's Disease: Beta-amyloid(1-42), Tau, Phospho-tau-181 and Total Protein*. Drugs of Today. 2007; 43(6):423-31.
Mattsson N, et al. *CSF biomarkers and incipient Alzheimer disease in patients with mild cognitive impairment JAMA*. 2009 Jul. 22; 302(4):385-93.
McKhann G, Drachman D, Folstein M, Katzman R, Price D, Stadlan E M. *Clinical Diagnosis of Alzheimer's Disease: Report of the NINCDS-ADRDA Work Group under the Auspices of Department of Health and Human Services Task Force on Alzheimer's Disease*. Neurology. 1984; 34(7):939-44.
Mölsä P K, Marttila R J, Rinne U K.; 1995 "*Long-term survival and predictors of mortality in Alzheimer's disease and multi-infarct dementia*." Acta Neurol Scand. 1995 March; 91(3):159-64.
O'Bryant, S. E., et al., *Guidelines for the standardization of preanalytic variables for blood-based biomarker studies in Alzheimer's disease research*. Alzheimers Dement, 2014.
Olson L. et al., "*Growth factors and cytokines/chemokines as surrogate biomarkers in cerebrospinal fluid and blood for diagnosing Alzheimer's disease and mild cognitive impairment*", Exp. Gerontol., vol. 45, no. 1, January 2010, pages 41-46.
Petersen R C, Smith G E, Waring S C, Ivnik R J, Tangalos E G, Kokmen E (1999). "*Mild cognitive impairment: clinical characterization and outcome*". Arch. Neurol. 56 (3): 303-8.
Schneider, P., H. Hampel, and K. Buerger, *Biological marker candidates of Alzheimer's disease in blood, plasma, and serum*. CNS Neurosci Ther, 2009. 15(4): p. 358-74.
Thal, L. J., et al., *The role of biomarkers in clinical trials for Alzheimer disease*. Alzheimer Dis Assoc Disord, 2006. 20(1): p. 6-15.
Tiraboschi P, Hansen L A, Thal L J, Corey-Bloom J. *The Importance of Neuritic Plaques and Tangles to the Development and Evolution of AD*. Neurology. 2004; 62(11): 1984-9.
Waldemar G, Dubois B, Emre M, Georges J, McKeith I G, Rossor M, Scheltens P, Tariska P, Winblad B. *Recommendations for the Diagnosis and Management of Alzheim-*

*er's Disease and Other Disorders Associated with Dementia: EFNS Guideline.* European Journal of Neurology. 2007; 14(1):e1-26.

The invention claimed is:

1. An in vitro or ex vivo method for assessing the cognitive function of a subject, wherein said method comprises a step of associating said subject to a cognitive status selected from Subjective Cognitive Impairment (SCI) and Mild Cognitive Impairment (MCI), and wherein said association results from the evaluation of glycosylated MCSF (Macrophage Colony Stimulating Factor) in a blood sample deprived of red blood cells from the subject, evaluation of CCR2 expressed on the surface of peripheral blood mononuclear cells (PBMCs) in a blood sample from the subject, and of at least one of IL-3 and CCL18 (PARC) in a blood sample from the subject, wherein the method comprises separating PBMCs from plasma in the blood sample and said evaluation step comprises detecting the presence of a marker, comparing the concentration of a marker to a reference value and/or comparing markers.

2. The method of claim 1, wherein the association results from the additional evaluation of CCL15 (MIP1-delta) and/or RANTES (CCL5).

3. The method of claim 1, wherein the method further comprises a step of selecting PBMCs expressing at least one surface marker selected from CD3, CD11c, CD14, CD4, CD8, CD25, CD27, CD33, CD38, CD62L, CD45RO, CD123, CD127, CD131, CD163, CD196 (CCR7) and CXCR3, and a step of detecting the presence of CCR2 at the surface of the selected PBMCs.

4. The method of claim 3, wherein the method comprises a step of separating CD3$^+$ PBMCs and Cd11c$^+$ PBMCs present in the biological sample.

5. The method of claim 4, wherein PBMCs are lymphocytes and/or dendritic cells.

6. The method of claim 3, wherein the method comprises a step of separating CD3$^+$ PBMCs, Cd11c$^+$ PBMCs and Cd11c$^-$ PBMCs present in the biological sample.

7. The method of claim 1, wherein the evaluation provides information for predicting the cognitive impairment progression within a SCI, a MCI and a neurodegenerative disease, is indicative of the responsiveness of the subject to a treatment, or is indicative of the efficacy of a treatment in the subject.

8. The method of claim 7, wherein the neurodegenerative disease is Alzheimer's disease (AD).

9. The method of claim 1, wherein said biological sample is from a mammal.

10. A method for selecting subjects eligible for a clinical study or trial for a neurodegenerative disease, the method comprising a step of assessing the cognitive function of a subject using the method according to claim 1.

11. The method of claim 10, wherein the neurodegenerative disease is dementia.

12. The method of claim 1, wherein said biological sample is from a human being.

13. An in vitro or ex vivo method for assessing the cognitive function of a subject, wherein said method comprises a step a) of determining whether said subject is suffering of Subjective Cognitive Impairment (SCI), said step a) comprising evaluating at least CCR2 expressed on the surface of PBMCs in a blood sample from the subject, and if the subject is not identified as suffering of SCI, a step b) of determining whether said subject is suffering of Mild Cognitive Impairment (MCI) said step b) comprising evaluating glycosylated MCSF together with CCL18, and optionally together with CCR2, in a sample deprived of red blood cells obtained from the blood sample from the subject, and if the subject is not identified as suffering of MCI, a step c) of determining whether said subject is suffering of AD, said step c) comprising evaluating CCL18 (PARC) and IL3 in a biological sample deprived of red blood cells from the subject, wherein the method comprises separating PBMCs from plasma obtained from the blood sample, and the evaluation step comprises determining the presence of a marker, comparing the concentration of a marker to a reference value and/or comparing markers.

14. The method of claim 13, wherein the sample deprived of red blood cells is a plasma or a serum sample.

15. The method of claim 13, wherein the method further comprises a step of administering to a subject identified as suffering of SCI or MCI a molecule selected from curcumin, a cyclophosphamide, a non-steroidal anti-inflammatory drug (NSAID) and an antibody directed against human IL-12 and IL-23.

16. A kit suitable for implementing a method for assessing the cognitive function of a subject, or for determining whether a subject is suffering of a cognitive impairment or of a neurodegenerative disease, or is at risk of developing such a neurodegenerative disease, wherein the kit comprises a capture agent binding specifically glycosylated MCSF, a capture agent binding specifically CCR2 expressed at the surface of PBMCs, and a capture agent binding at least one of IL-3 and CCL18 (PARC); and instructions for carrying out the method.

17. The kit of claim 16, wherein the kit further comprises at least one capture agent binding CCL15 (MIP1-delta) or binding RANTES (CCL5).

18. The kit of claim 16, wherein PBMC is a PBMC expressing a surface marker selected from CD3, CD11c, CD14, CD4, CD8, CD25, CD27, CD33, CD38, CD62L, CD45RO, CD123, CD127, CD131, CD163, CD196 (CCR7), CXCR3 and a combination thereof.

19. The kit of claim 16, wherein the kit further comprises a solid support comprising capture agent(s) attached thereto.

20. The kit of claim 16, wherein PBMCs are selected from PBMCs expressing a combination of at least two of CD3, CD11c and CD14.

21. A kit for assessing whether a subject suffering of SCI or MCI is at risk of developing AD, wherein the kit comprises a capture agent binding specifically CCR2 expressed at the surface of PBMCs and a capture agent binding specifically glycosylated MCSF.

* * * * *

UNITED STATES PATENT AND TRADEMARK OFFICE
CERTIFICATE OF CORRECTION

PATENT NO. : 10,527,634 B2
APPLICATION NO. : 15/553186
DATED : January 7, 2020
INVENTOR(S) : Nicolas Pelletier, Philippe Compagnone and Nathalie Compagnone Page 1 of 1

It is certified that error appears in the above-identified patent and that said Letters Patent is hereby corrected as shown below:

In the Specification

<u>Column 19,</u>
Line 19, "pruning Several" should read --pruning. Several--.

Signed and Sealed this
Sixteenth Day of June, 2020

Andrei Iancu
*Director of the United States Patent and Trademark Office*